United States Patent
Dykstra et al.

(10) Patent No.: US 6,887,838 B2
(45) Date of Patent: May 3, 2005

(54) BLEACH BOOSTING COMPONENTS, COMPOSITIONS AND LAUNDRY METHODS

(75) Inventors: Robert Richard Dykstra, Cleves, OH (US); Gregory Scot Miracle, Hamilton, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/854,696

(22) Filed: May 26, 2004

(65) Prior Publication Data

US 2004/0220069 A1 Nov. 4, 2004

Related U.S. Application Data

(63) Continuation of application No. 10/069,628, filed as application No. PCT/US00/23322 on Aug. 25, 2000, now Pat. No. 6,818,607.
(60) Provisional application No. 60/151,173, filed on Aug. 27, 1999.

(51) Int. Cl.$^7$ .............................. C11D 3/26; C11D 3/39; C11D 3/395
(52) U.S. Cl. ........................ 510/314; 510/303; 510/305; 510/310; 510/336; 510/337; 510/372; 510/376; 510/504; 540/472; 540/479; 540/544; 540/547; 540/548; 540/557
(58) Field of Search ................................ 510/303, 304, 510/309, 310, 314, 336, 337, 351, 352, 372, 376, 504; 8/111, 137; 540/472, 479, 544, 547, 548, 557

(56) References Cited

U.S. PATENT DOCUMENTS

| | | |
|---|---|---|
| 4,096,141 A | 6/1978 | Milkowski et al. |
| 4,194,987 A | 3/1980 | Brubaker |
| 4,325,957 A | 4/1982 | Zeugner et al. |
| 4,505,908 A | 3/1985 | Zeugner et al. |
| 4,595,531 A | 6/1986 | Milkowski et al. |
| 5,041,232 A | 8/1991 | Batal et al. |
| 5,045,223 A | 9/1991 | Batal et al. |
| 5,047,163 A | 9/1991 | Batal et al. |
| 5,310,925 A | 5/1994 | Batal et al. |
| 5,360,568 A | 11/1994 | Madison et al. |
| 5,360,569 A | 11/1994 | Madison et al. |
| 5,370,826 A | 12/1994 | Madison et al. |
| 5,413,733 A | 5/1995 | Nicholson et al. |
| 5,442,066 A | 8/1995 | Madison et al. |
| 5,478,357 A | 12/1995 | Madison et al. |
| 5,482,515 A | 1/1996 | Madison et al. |
| 5,550,256 A | 8/1996 | Madison et al. |
| 5,576,282 A | 11/1996 | Miracle et al. |
| 5,652,207 A | 7/1997 | Ghatlia |
| 5,693,603 A | 12/1997 | Ghatlia |
| 5,710,116 A | 1/1998 | Miracle et al. |
| 5,753,599 A | 5/1998 | Coope et al. |
| 5,760,222 A | 6/1998 | Coope |
| 5,817,614 A | 10/1998 | Miracle et al. |
| 5,952,282 A | 9/1999 | Löffler et al. |
| 6,007,583 A | 12/1999 | Nestler |
| 6,120,557 A | 9/2000 | Nestler |
| 6,818,607 B1 | 11/2004 | Dykstra |
| 6,821,935 B1 | 11/2004 | Dykstra |
| 6,825,160 B1 | 11/2004 | Dykstra |

FOREIGN PATENT DOCUMENTS

| | | |
|---|---|---|
| CA | 1122980 | 5/1982 |
| WO | WO 95/13351 | 5/1995 |
| WO | WO 95/13352 | 5/1995 |
| WO | WO 95/13353 | 5/1995 |
| WO | WO 95/28399 | 10/1995 |
| WO | WO 97/06147 | 2/1997 |
| WO | WO 98/07825 | 2/1998 |
| WO | WO 98/15535 | 4/1998 |
| WO | WO 98/23602 | 6/1998 |
| WO | WO 98/23717 | 6/1998 |

OTHER PUBLICATIONS

U.S. Appl. No. 10/069,635, filed Feb. 26, 2002, Dykstra.
U.S. Appl. No. 10/969,634, filed Feb. 26, 2002, Dykstra.
U.S. Appl. No. 10/069,632, filed Feb. 26, 2002, Dykstra.
U.S. Appl. No. 10/069,633, filed Feb. 26, 2002, Dykstra.
U.S. Appl. No. 10/069,631, filed Feb. 26, 2002, Dykstra.
U.S. Appl. No. 10/083,948, filed Feb. 27, 2002, Dykstra.
U.S. Appl. No. 10/069,629, filed Feb. 26, 2002, Dykstra.
H. Böhme et al., *Uber Derivate des 1,2,3,4, 5–Pentahydro–2–benzazepins*, Arch Pharm, vol. 306 (4), 1972, pp. 271–274.

*Primary Examiner*—Gregory R. Del Cotto
(74) *Attorney, Agent, or Firm*—James F. MeBride; Kim W. Zerby; Steve W. Miller

(57) ABSTRACT

Formulation components such as bleach boosting compounds selected from the group consisting of bleach boosters comprising quaternary imine cations, zwitterions, polyions having a net charge of from about +3 to about 3 and mixtures thereof, bleaching species comprising oxariridinium cations, zwitterions, polyions having a net charge of from about +3 to about −3 and mixtures thereof, and mixtures thereof are disclosed. The bleach boosting compounds increase bleaching effectiveness even in lower temperature solutions and provides improved stability toward unwanted boosting compound decomposition. The bleach boosting compounds are ideally suited for inclusion into bleaching compositions including those with detersive surfactants and enzymes. Also provided is a method for laundering a fabric employing the bleach compounds, a laundry additive product employing the bleach boosting compounds.

19 Claims, No Drawings

SEQUENCE LISTING

<160> NUMBER OF SEQ ID NOS: 18

<210> SEQ ID NO 1
<211> LENGTH: 21
<212> TYPE: DNA
<213> ORGANISM: Aspergillus aculeatus

<400> SEQUENCE: 1
attcatttgt ggacagtgga c                       21

<210> SEQ ID NO 2
<211> LENGTH: 20
<212> TYPE: DNA
<213> ORGANISM: Aspergillus aculeatus

<400> SEQUENCE: 2
gttgatcgca cattgaacca                          20

```
<210> SEQ ID NO 3
<211> LENGTH: 20
<212> TYPE: DNA
<213> ORGANISM: Aspergillus aculeatus

<400> SEQUENCE: 3
accccagccg accgattgtc                                                  20

<210> SEQ ID NO 4
<211> LENGTH: 20
<212> TYPE: DNA
<213> ORGANISM: Aspergillus aculeatus

<400> SEQUENCE: 4
cttccttacc tcaccatcat                                                  20

<210> SEQ ID NO 5
<211> LENGTH: 20
<212> TYPE: DNA
<213> ORGANISM: Aspergillus aculeatus

<400> SEQUENCE: 5
ttaacatctt ttcaccatga                                                  20

<210> SEQ ID NO 6
<211> LENGTH: 20
<212> TYPE: DNA
<213> ORGANISM: Aspergillus aculeatus

<400> SEQUENCE: 6
agctttccct tctctccctt                                                  20

<210> SEQ ID NO 7
<211> LENGTH: 28
<212> TYPE: DNA
<213> ORGANISM: Aspergillus aculeatus

<400> SEQUENCE: 7
gccaccctgg cttccgctgc cagcctcc                                         28

<210> SEQ ID NO 8
<211> LENGTH: 20
<212> TYPE: DNA
<213> ORGANISM: Aspergillus aculeatus

<400> SEQUENCE: 8
gacagtagca atccagcatt                                                  20

<210> SEQ ID NO 9
<211> LENGTH: 20
<212> TYPE: DNA
<213> ORGANISM: Aspergillus aculeatus

<400> SEQUENCE: 9
agcatcagcc gctttgtaca                                                  20

<210> SEQ ID NO 10
<211> LENGTH: 20
<212> TYPE: DNA
<213> ORGANISM: Aspergillus aculeatus

<400> SEQUENCE: 10
```

```
ccatgaagtt caccgtattg                                               20

<210> SEQ ID NO 11
<211> LENGTH: 20
<212> TYPE: DNA
<213> ORGANISM: Aspergillus aculeatus

<400> SEQUENCE: 11
gcactgcttc tctcccaggt                                               20

<210> SEQ ID NO 12
<211> LENGTH: 20
<212> TYPE: DNA
<213> ORGANISM: Aspergillus aculeatus

<400> SEQUENCE: 12
gtgggcggcc cctcaggcaa                                               20

<210> SEQ ID NO 13
<211> LENGTH: 20
<212> TYPE: DNA
<213> ORGANISM: Aspergillus aculeatus

<400> SEQUENCE: 13
acgctcctcc aattttctct                                               20

<210> SEQ ID NO 14
<211> LENGTH: 19
<212> TYPE: DNA
<213> ORGANISM: Aspergillus aculeatus

<400> SEQUENCE: 14
ggctggtagt aatgagtct                                                19

<210> SEQ ID NO 15
<211> LENGTH: 20
<212> TYPE: DNA
<213> ORGANISM: Aspergillus aculeatus

<400> SEQUENCE: 15
ggcgcagagt ttggccaggc                                               20

<210> SEQ ID NO 16
<211> LENGTH: 21
<212> TYPE: DNA
<213> ORGANISM: Aspergillus aculeatus

<400> SEQUENCE: 16
caacatcccc ggtgttctgg g                                             21

<210> SEQ ID NO 17
<211> LENGTH: 347
<212> TYPE: DNA
<213> ORGANISM: Aspergillus aculeatus

<400> SEQUENCE: 17
aaagattcat ttgtggacag tggacgttga tcgcacattg aaccaacccc agccgaccga    60
ttgtccttcc ttacctcacc atcatttaac atcttttcac catgaagctt tcccttctct   120
cccttgccac cctggcttcc gctgccagcc tccagcgccg cacacttctg cggtcagtgg   180
gataccgcca ccgccggtga cttcaccctg tacaacgacc tttggggcga gacggccggc   240
accggctccc agtgcactgg agtcgactcc tacagcggcg acaccatcgc ttgtcacacc   300
```

-continued

```
agcaggtcct ggtcggagta gcagcagcgt caagagctat gccaacg        347

<210> SEQ ID NO 18
<211> LENGTH: 294
<212> TYPE: DNA
<213> ORGANISM: Aspergillus aculeatus

<400> SEQUENCE: 18
cagcatctcc attgagtaat cacgttggtg ttcggtggcc cgccgtgttg cgtggcggag   60
gctgccggga gacgggtggg gatggtggtg ggagagaatg tagggcgccg tgtttcagtc  120
cctaggcagg ataccggaaa accgtgtggt aggaggttta taggtttcca ggagacgctg  180
tataggggat aaatgagatt gaatggtggc cacactcaaa ccaaccaggt cctgtacata  240
caatgcatat accaattata cctaccaaaa aaaaaaaaaa aaaaaaaaaa aaaa        294
```

BLEACH BOOSTING COMPONENTS, COMPOSITIONS AND LAUNDRY METHODS

This application is a continuation of U.S. application Ser. No. 10/069,628, filed Feb. 26, 2002, now U.S. Pat. No. 6,818,607, which is a 371 of PCT/US00/23322, filed Aug. 25, 2000, which claims priority under 35 USC 119(e) to U.S. Provisional Application 60/151,173, filed Aug. 27, 1999.

FIELD OF THE INVENTION

This invention relates to formulation components such as bleach boosting compounds with increased stability, compositions and laundry methods employing bleach boosting compounds with increased stability. More particularly, this invention relates to quaternary imine bleach boosters and/or oxaziridinium bleaching species, compositions and laundry methods employing quaternary imine bleach boosters and/or oxaziridinium bleaching species.

BACKGROUND OF THE INVENTION

Oxygen bleaching agents have become increasingly popular in recent years in household and personal care products to facilitate stain and soil removal. Bleaches are particularly desirable for their stain-removing, dingy fabric cleanup, whitening and sanitization properties. Oxygen bleaching agents have found particular acceptance in laundry products such as detergents, in automatic dishwashing products and in hard surface cleansers. Oxygen bleaching agents, however, are somewhat limited in their effectiveness. Some frequently encountered disadvantages include color damage on fabrics and damage to laundry appliances. In addition, oxygen bleaching agents tend to be extremely temperature rate dependent. Thus, the colder the solution in which they are employed, the less effective the bleaching action. Temperatures in excess of 60° C. are typically required for effectiveness of an oxygen bleaching agent in solution.

To solve the aforementioned temperature rate dependency, a class of compounds known as "bleach activators" has been developed. Bleach activators, typically perhydrolyzable acyl compounds having a leaving group such as oxybenzenesulfonate, react with the active oxygen group, typically hydrogen peroxide or its anion, to form a more effective peroxyacid oxidant. It is the peroxyacid compound which then oxidizes the stained or soiled substrate material. However, bleach activators are also somewhat temperature dependent. Bleach activators are more effective at warm water temperatures of from about 40° C. to about 60° C. In water temperatures of less than about 40° C., the peroxyacid compound loses some of its bleaching effectiveness.

Attempts have been made as disclosed in U.S. Pat. Nos. 5,360,568, 5,360,569 and 5,370,826 all to Madison et al. to develop a bleach system which is effective in lower temperature water conditions. However, the dihydroisoquinolinium bleach boosters disclosed in these references, when combined with peroxygen compounds, undergo undesired decomposition, including the formation of an inactive, aromatic isoquinolinium, which causes a reduction in booster efficiency.

In light of the foregoing, researchers have been pursuing with vim and vigor effective bleach boosting agents that do not undergo decomposition.

Accordingly, the need remains for effective bleach boosting compounds and compositions containing bleach boosting compounds which provide effective bleaching even in lower water temperatures and provide improved stability toward unwanted bleach boosting compound decomposition.

SUMMARY OF THE INVENTION

This need is met by the present invention wherein longer lasting bleach boosting compounds, specifically bleach boosters and/or bleaching species are provided. The bleach boosting compounds of the present invention provide superior bleaching effectiveness even in lower water temperatures.

A bleaching composition comprising a bleach boosting compound in conjunction with or without a peroxygen source, wherein said bleach boosting compound is selected from the group consisting of: (a) a bleach booster selected from the group consisting of aryliminium cations, aryliminium zwitterions, aryliminium polyions having a net charge of from about +3 to about −3 and mixtures thereof; (b) a bleaching species selected from the group consisting of oxaziridinium cations, oxaziridinium zwitterions, oxaziridinium polyions having a net charge of from about +3 to about −3 and mixtures thereof; and (c) mixtures thereof is provided in a first embodiment.

In accordance with another embodiment of the present invention, a cationic or zwitterionic laundry bleach boosting compound is provided.

In accordance with still another aspect of the present invention, a method for laundering a fabric in need of laundering comprising contacting the fabric with a laundry solution having a bleaching composition in accordance with the present invention as described herein is provided.

In accordance with still yet another aspect of the present invention, a laundry additive product comprising a bleach boosting compound selected from the group consisting of: (a) a bleach booster selected from the group consisting of aryliminium cations, aryliminium zwitterions, aryliminium polyions having a net charge of from about +3 to about −3 and mixtures thereof, (b) a bleaching species selected from the group consisting of oxaziridinium cations, oxaziridinium zwitterions, oxaziridinium polyions having a net charge of from about +3 to about −3 and mixtures thereof; and (c) mixtures thereof is provided.

Accordingly, it is an object of the present invention to provide: a bleach boosting compound which demonstrates improved performance even in lower temperature solutions as well as precluding unwanted aromatization; a bleaching composition including a quaternary imine bleach booster and/or an oxaziridinium bleaching species; a method for laundering a fabric by employing a quaternary imine bleach booster and/or an oxaziridinium bleaching species; and a laundry additive product having a quaternary imine bleach booster and/or an oxaziridinium bleaching species. These, and other objects, features and advantages of the present invention will be recognized by one of ordinary skill in the art from the following description and the appended claims.

All percentages, ratios and proportions herein are on a weight basis unless otherwise indicated. All documents cited herein are hereby incorporated by reference.

DETAILED DESCRIPTION OF THE INVENTION

The present invention discloses novel and highly useful bleach boosting compounds ("bleach boosters", "bleaching species" and mixtures thereof), compositions, and methods employing the novel bleach boosting compounds. The bleach boosting compounds of the present invention provide increased bleaching effectiveness even in lower temperature applications while precluding unwanted decomposition by aromatization, resulting in improved performance. The bleach boosting compounds of the present invention act in conjunction with or without, preferably with conventional peroxygen bleaching sources to provide the above-mentioned increased bleaching effectiveness and preclude aromatization.

Definitions

"Peroxygen source" as used herein means materials that generate peroxygen compounds, which can include the peroxygen compounds themselves. Examples include, but are not limited to, bleach activators, peracids, percarbonate, perborate, hydrogen peroxide, bleach boosting compounds, and/or bleaching species (e.g., oxaziridiniums).

"Peroxygen compounds" as used herein includes peracids and peroxides (e.g., hydrogen peroxide, alkyl hydroperoxides, etc.

"Peracid" as used herein means a peroxyacid such as peroxycarboxylic acid and/or peroxymonosulfuric acid (tradname OXONE) and their salts.

Bleach Boosters—The bleach boosters, preferably quaternary imine bleach boosters, of the present invention have the formulas [I] and [II]:

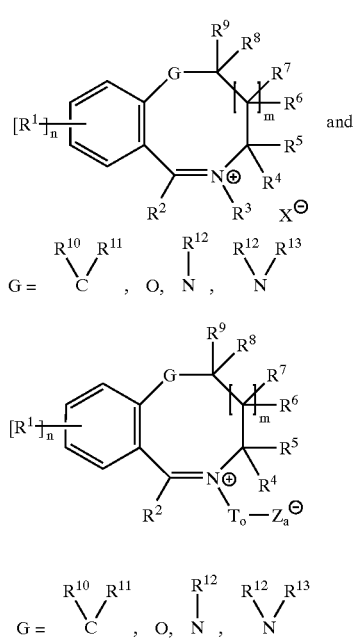

wherein: m is 0 or 1 and n is an integer from 0 to 4; each $R^1$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^1$ substituents may combine to form a fused aryl, fused carbocyclic or fused heterocyclic ring; $R^2$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^3$ may be a substituted or unsubstituted, saturated or unsaturated, radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of $-CO_2^-$, $-SO_3^-$, $-OSO_3^-$, $-SO_2^-$ and $-OSO_2^-$ and a is either 1 or 2; $T_o$ is selected from the group consisting of: (1) $-(CH(R^{14}))-$ or $-(C(R^{14})_2)-$ wherein $R^{14}$ is independently selected from H or $C_1$–$C_8$ alkyl; (2) $-CH_2(C_6H_4)-$;

(3)
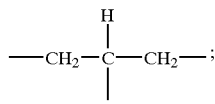

(4)
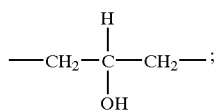

(5) $-(CH_2)_d(E)(CH_2)_f-$ wherein d is from 2 to 8, f is from 1 to 3 and E is $-C(O)O-$;

(6) $-C(O)NR^{15}-$ wherein $R^{15}$ is H or $C_1$–$C_4$ alkyl;

(7)
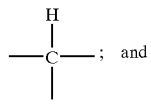 ; and (8)
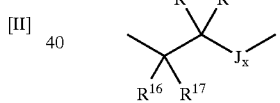

wherein x is equal to 0–3; J, when present, is independently selected from the group consisting of $-CR^{20}R^{21}-$, $-CR^{20}R^{21}CR^{22}R^{23}-$, and $-CR^{20}R^{21}CR^{22}R^{23}CR^{24}R^{25}-$; $R^{16}$–$R^{25}$ are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^4$–$R^{11}$ are substituted or unsubstituted radicals independently selected from the group consisting of H, linear or branched $C_1$–$C_{12}$ alkyls, alkylenes, alkoxys, aryls, alkaryls, aralkyls, cycloalkyls, and heterocyclic rings, and $R^{12}$ and $R^{13}$ are substituted or unsubstituted radicals independently selected from the group consisting of H, oxygen, linear or branched $C_1$–$C_{12}$ alkyls, alkylenes, alkoxys, aryls, alkaryls, aralkyls, cycloalkyls, and heterocyclic rings; provided that any of $R^1$–$R^{13}$ may be joined together with any other of $R^1$–$R^{13}$ to form part of a common ring; any geminal $R^4$–$R^{11}$ may combine to form a carbonyl as in the following examples in which $R^8$–$R^9$ combine to form a carbonyl:

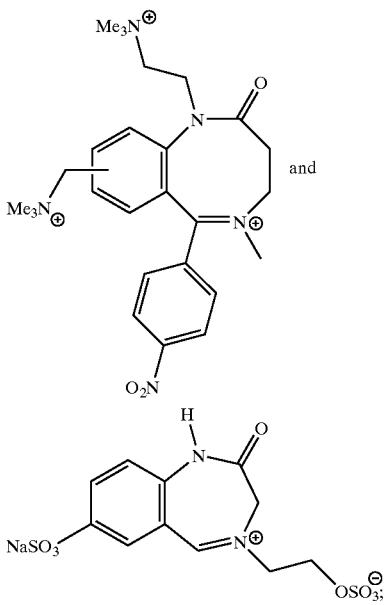

and

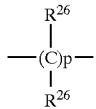

any vicinal $R^4$–$R^{13}$ may join to form unsaturation; and wherein any one group of substituents $R^4$–$R^7$, $R^6$–$R^9$, or $R^8$–$R^{13}$ may combine to form a substituted or unsubstituted fused unsaturated moiety.

Preferred bleach boosters include, but are not limited to: (1) aryliminium cations of formula [I] wherein $R^2$ is H or methyl, and $R^3$ is H or linear or branched $C_1$–$C_{14}$ substituted or unsubstituted alkyl; (2) aryliminium zwitterions of formula [II] wherein $R^2$ is H or methyl, and $R^3$ has the formula:

wherein $Z^-$ is —$CO_2^-$, —$SO_3^-$ or —$OSO_3^-$, and a is 1; (3) aryliminium cations of formula [I] wherein $R^3$ is selected from the group consisting of a linear or branched $C_1$–$C_{14}$ substituted or unsubstituted alkyl, or aryliminium zwitterions of formula [II] wherein $R^3$ is a radical represented by the formula:

wherein $Z^-$ is —$CO_2^-$, —$SO_3^-$ or —$OSO_3^-$, a is 1 and $T_o$ is selected from the group consisting of:

$$-(C)_p-\begin{matrix}R^{26}\\|\\|\\R^{26}\end{matrix}$$

wherein p is an integer from 2 to 4, and $R^{26}$ is independently selected from the group consisting of H and linear or branched $C_1$–$C_{18}$ substituted or unsubstituted alkyl; and (4) aryliminium polyions having a net negative charge wherein $R^2$ is H, Z is —$CO_2^-$, —$SO_3^-$ or —$OSO_3^-$ and a is 2.

The 7- or 8-membered ring bleach boosters, unlike 6-membered ring bleach boosters, do not require geminal substitution to inhibit or prevent aromatization decomposition. The aromatization (decomposition) reaction of 6-membered ring boosters is well known in the art, as exemplified, without being limited by theory, in Hanquet et al., *Tetrahedron* 1993, 49, pp. 423–438. The 7- or 8-membered ring bleach boosters cannot undergo the based-induced aromatization, and thus any aromatization-promoted loss of turnover number associated with the catalytic cycle of the bleach booster/bleaching species system is avoided. The 7- or 8-membered ring bleach boosters, without being limited by theory, may also inhibit or prevent decomposition of the cations, zwitterions, and polyions via other decomposition pathways. Other means of decomposition include, but are not limited to, attack on the bleach boosting compound and/or on the bleaching species by nucleophiles, including but not limited to attack by hydroxide anion, perhydroxide anion, carboxylate anion, percarboxylate anion and other nucleophiles present under in-wash conditions.

The quaternary imine bleach boosters of the present invention act in conjunction with the peroxygen source to provide a more effective bleaching system. Peroxygen sources are well-known in the art and the peroxygen source employed in the present invention may comprise any of these well known sources, including peroxygen compounds as well as compounds which under consumer use conditions provide an effective amount of peroxygen in situ. The peroxygen source may include a hydrogen peroxide source with or without a bleach activator, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention.

The hydrogen peroxide source may be any suitable hydrogen peroxide source and present at such levels as filly described in U.S. Pat. No. 5,576,282. For example, the hydrogen peroxide source may be selected from the group consisting of perborate compounds, percarbonate compounds, perphosphate compounds and mixtures thereof.

The bleach activator may be selected from the group consisting of tetraacetylethylenediamine, sodium octanoyloxybenzene sulfonate, sodium nonanoyloxybenzene sulfonate, sodium decanoyloxybenzene sulfonate, sodium lauroyloxybenzene sulfonate, (6-octanamido-caproyl) oxybenzenesulfonate, (6-nonanamido-caproyl) oxybenzenesulfonate, (6-decanamido-caproyl) oxybenzenesulfonate, and mixtures thereof.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters, 4-[N-(nonaoyl) amino hexanoyloxy]-benzene sulfonate sodium salt (NACA-OBS) an example of which is described in U.S. Pat. No. 5,523,434, lauroyloxybenzenesulfonate or dodecanoyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA) and mixtures thereof, most preferably benzoylcaprolactam and benzoylvalerolactam. Particularly preferred bleach activators in the pH range from about 8 to about 9.5 are those selected having an OBS or VL leaving group.

Other preferred bleach activators are those described in U.S. Pat. No. 5,698,504 Christie et al., issued Dec. 16, 1997; U.S. Pat. No. 5,695,679 Christie et al. issued Dec. 9, 1997; U.S. Pat. No. 5,686,401 Willey et al., issued Nov. 11, 1997; U.S. Pat. No. 5,686,014 Hartshorn et al., issued Nov. 11, 1997; U.S. Pat. No. 5,405,412 Willey et al., issued Apr. 11, 1995; U.S. Pat. No. 5,405,413 Willey et al., issued Apr. 11, 1995; U.S. Pat. No. 5,130,045 Mitchel et al., issued Jul. 14, 1992; and U.S. Pat. No. 4,412,934 Chung et al., issued Nov. 1, 1983, and copending patent applications U.S. Ser. Nos. 08/709,072, 08/064,564, all of which are incorporated herein by reference.

Quaternary substituted bleach activators may also be included. The present detergent compositions preferably comprise a quaternary substituted bleach activator (QSBA) or a quaternary substituted peracid (QSP); more preferably, the former. Preferred QSBA structures are further described in U.S. Pat. No. 5,686,015 Willey et al., issued Nov. 11, 1997; U.S. Pat. No. 5,654,421 Taylor et al., issued Aug. 5, 1997; U.S. Pat. No. 5,460,747 Gosselink et al., issued Oct. 24, 1995; U.S. Pat. No. 5,584,888 Miracle et al., issued Dec. 17, 1996; and U.S. Pat. No. 5,578,136 Taylor et al., issued Nov. 26, 1996; all of which are incorporated herein by reference.

Highly preferred bleach activators useful herein are amide-substituted as described in U.S. Pat. No. 5,698,504, U.S. Pat. No. 5,695,679, and U.S. Pat. No. 5,686,014 each of which are cited herein above. Preferred examples of such bleach activators include: (6-octanamidocaproyl) oxybenzenesulfonate, (6-nonanamidocaproyl) oxybenzenesulfonate, (6-decanamidocaproyl) oxybenzenesulfonate and mixtures thereof.

Other useful activators, disclosed in U.S. Pat. No. 5,698,504, U.S. Pat. No. 5,695,679, U.S. Pat. No. 5,686,014 each of which is cited herein above and U.S. Pat. No. 4,966,723 Hodge et al., issued Oct. 30, 1990, include benzoxazin-type activators, such as a $C_6H_4$ ring to which is fused in the 1,2-positions a moiety —C(O)OC($R^1$)=N—.

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. No. 5,698,504, U.S. Pat. No. 5,695,679 and U.S. Pat. No. 5,686,014, each of which is cited herein above, are very useful herein, especially the acyl caprolactams (see for example WO 94-28102 A) and acyl valerolactams (see U.S. Pat. No. 5,503,639 Willey et al., issued Apr. 2, 1996 incorporated herein by reference).

The preformed peracid compound as used herein is any convenient compound which is stable and which under consumer use conditions provides an effective amount of peracid anion. The bleach boosters of the present invention may of course be used in conjunction with a preformed peracid compound selected from the group consisting of percarboxylic acids and salts, percarbonic acids and salts, perimidic acids and salts, peroxymonosulfuric acids and salts, and mixtures thereof, examples of which are described in U.S. Pat. No. 5,576,282 to Miracle et al.

One class of suitable organic peroxycarboxylic acids have the general formula:

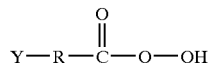

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

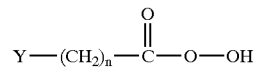

where Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

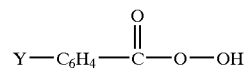

wherein Y can be, for example, hydrogen, alkyl, alkylhalogen, halogen, C(O)OH or C(O)OOH.

Typical monoperoxy acids useful herein include alkyl and aryl peroxyacids such as:

(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);

(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);

(iii) amidoperoxyacids, e.g. monononylamide of either peroxysuccinic acid (NAPSA) or of peroxyadipic acid (NAPAA).

Typical diperoxyacids useful herein include alkyl diperoxyacids and aryldiperoxyacids, such as:

(iv) 1,12-diperoxydodecanedioic acid;
(v) 1,9-diperoxyazelaic acid;
(vi) diperoxybrassylic acid; diperoxysebacic acid and diperoxyisophthalic acid;
(vii) 2-decyldiperoxybutane-1,4-dioic acid;
(viii) 4,4'-sulfonylbisperoxybenzoic acid.

Such bleaching agents are disclosed in U.S. Pat. No. 4,483,781, Hartman, issued Nov. 20, 1984, U.S. Pat. No. 4,634,551 to Bums et al., European Patent Application 0,133,354, Banks et al. published Feb. 20, 1985, and U.S. Pat. No. 4,412,934, Chung et al. issued Nov. 1, 1983. Sources also include 6-nonylamino-6-oxoperoxycaproic acid as fully described in U.S. Pat. No. 4,634,551, issued Jan. 6, 1987 to Burns et al. Persulfate compounds such as for example OXONE, manufactured commercially by E.I. DuPont de Nemours of Wilmington, Del. can also be employed as a suitable source of peroxymonosulfuric acid A bleach activator as used herein is any compound which when used in conjunction with a hydrogen peroxide source leads to the in situ production of the peracid corresponding to the bleach activator. Various non limiting examples of activators are fully disclosed in U.S. Pat. No. 5,576,282, U.S. Pat. No. 4,915,854 and U.S. Pat. No. 4,412,934. See also U.S. Pat. No. 4,634,551 for other typical bleaches and activators useful herein.

The quaternary imine bleach booster of the present invention acts in conjunction with a peroxygen source to increase bleaching effectiveness. Without being bound by theory, it is believed that the bleach booster reacts with the peroxygen source to form a more active bleaching species, a quaternary oxaziridinium compound. The oxaziridinium compound has an increased activity at lower temperatures relative to the peroxygen compound. The oxaziridinium compound is represented by the formulas [III] and [IV]:

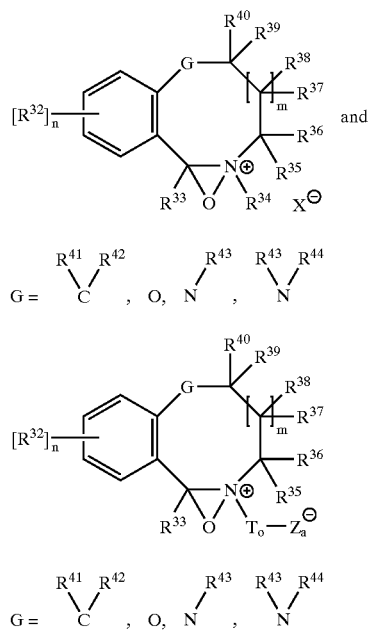

wherein: m is 0 or 1 and wherein n is an integer from 0 to 4; each $R^{32}$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^{32}$ substituents may combine to form a fused aryl, fused carbocyclic or fused heterocyclic ring; $R^{33}$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^{34}$ may be a substituted or unsubstituted radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of $-CO_2^-$, $-SO_3^-$, $-OSO_3^-$, $-SO_2^-$ and $-OSO_2^-$ and a is either 1 or 2; $T_o$ is selected from the group consisting of: (1) $-(CH(R^{45}))-$ or $-(C(R^{45})_2)-$ wherein $R^{45}$ is independently selected from H or $C_1-C_8$ alkyl; (2) $-CH_2(C_6H_4)-$; (3) $-(CH_2)_d(E)(CH_2)_f-$ wherein d is from 2 to 8, f is from 1 to 3 and E is $-C(O)O-$; (4) $-C(O)NR^{46}-$ wherein $R^{46}$ is H or $C_1-C_4$ alkyl; and

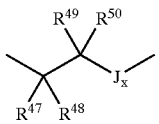

wherein x is equal to 0–3; J, when present, is independently selected from the group consisting of $-CR^{51}R^{52}-$, $-CR^{51}R^{52}CR^{53}R^{54}-$, and $-CR^{51}R^{52}CR^{53}R^{54}CR^{55}R^{56}-$; $R^{47}-R^{56}$ are substituted or unsubstituted radicals selected from the linear or branched group consisting of H, $C_1-C_{18}$ alkyls, cycloalkyls, alkaryls, aryls, aralkyls, alkylenes, heterocyclic rings, alkoxys, arylcarbonyls, carboxyalkyls and amide groups; $R^{32}-R^{42}$ are substituted or unsubstituted radicals independently selected from the group consisting of H, linear or branched $C_1-C_{12}$ alkyls, alkylenes, alkoxys, aryls, alkaryls, aralkyls, cycloalkyls, and heterocyclic rings, and $R^{43}$ and $R^{44}$ are substituted or unsubstituted radicals independently selected from the group consisting of H, oxygen, linear or branched $C_1-C_{12}$ alkyls, alkylenes, alkoxys, aryls, alkaryls, aralkyls, cycloalkyls, and heterocyclic rings, further provided that any of $R^{32}-R^{44}$ may be joined together with any other of $R^{32}-R^{44}$ to form part of a common ring; any vicinal $R^{35}-R^{44}$ may join to form unsaturation; and wherein any one group of substituents $R^{35}-R^{38}$, $R^{37}-R^{40}$, $R^{39}-R^{42}$ or $R^{43}$ and $R^{44}$, when present, may combine to form a substituted or unsubstituted fused unsaturated moiety.

Furthermore, $R^{32}-R^{56}$ of the bleaching species of formulas [III] and [IV] may be the same as $R^1-R^{25}$ of the bleach booster of formulas [I] and [II], respectively. Such oxaziridinium compounds can be produced from the quaternary imine of the present invention with the reactions:

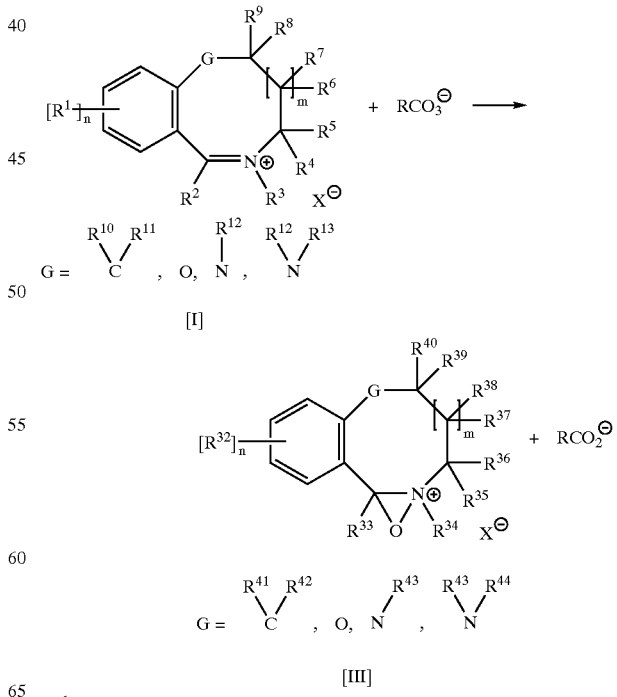

and

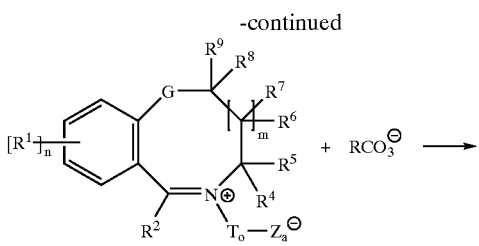

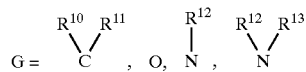

[II]

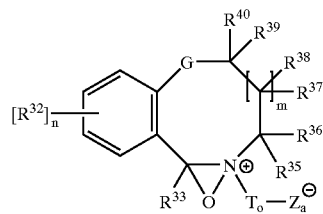

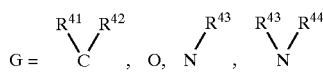

Bleaching Species—The bleaching species (oxaziridiniums) may also be used directly in accordance with the present invention. The bleaching species of the present invention have the formulas [III] and [IV]:

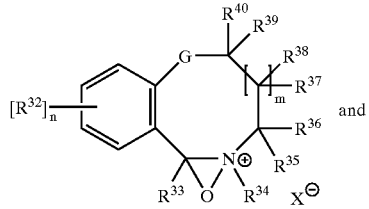

[III]

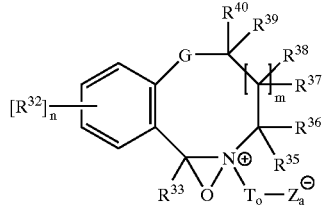

[IV]

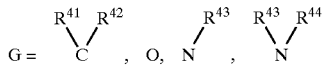

wherein: m is 0 or 1 and wherein n is an integer from 0 to 4; each $R^{32}$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals and any two vicinal $R^{32}$ substituents may combine to form a fused aryl, fused carbocyclic or fused heterocyclic ring; $R^{33}$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^{34}$ may be a substituted or unsubstituted radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of $-CO_2^-$, $-SO_3^-$, $-OSO_3^-$, $-SO_2^-$ and $-OSO_2^-$ and a is either 1 or 2; $T_o$ is selected from the group consisting of: (1) $-(CH(R^{45}))-$ or $-(C(R^{45})_2)-$ wherein $R^{45}$ is independently selected from H or $C_1$–$C_8$ alkyl; (2) $-CH_2(C_6H_4)-$; (3) $-(CH_2)_d(E)(CH_2)_f-$ wherein d is from 2 to 8, f is from 1 to 3 and E is $-C(O)O-$; (4) $-C(O)NR^{46}-$ wherein $R^{46}$ is H or $C_1$–$C_4$ alkyl; and

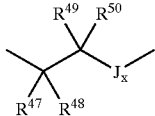

(5)

wherein x is equal to 0–3; J, when present, is independently selected from the group consisting of $-CR^{51}R^{52}-$, $-CR^{51}R^{52}CR^{53}R^{54}-$, and $-CR^{51}R^{52}CR^{53}R^{54}CR^{55}R^{56}-$; $R^{47}$–$R^{56}$ are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^{35}$–$R^{42}$ are substituted or unsubstituted radicals independently selected from the group consisting of H, linear or branched $C_1$–$C_{12}$ alkyls, alkylenes, alkoxys, aryls, alkaryls, aralkyls, cycloalkyls, and heterocyclic rings, and $R^{43}$ and $R^{44}$ are substituted or unsubstituted radicals independently selected from the group consisting of H, oxygen, linear or branched $C_1$–$C_{12}$ alkyls, alkylenes, alkoxys, aryls, alkaryls, aralkyls, cycloalkyls, and heterocyclic rings, further provided that any of $R^{32}$–$R^{44}$ may be joined together with any other of $R^{32}$–$R^{44}$ to form part of a common ring; any vicinal $R^{35}$–$R^{44}$ may join to form unsaturation; and wherein any one group of substituents $R^{35}$–$R^{38}$, $R^{37}$–$R^{40}$, $R^{39}$–$R^{42}$ or $R^{43}$ and $R^{44}$, when present, may combine to form a substituted or unsubstituted fused unsaturated moiety.

Preferred bleaching species include, but are not limited to: (1) oxaziridinium cations or oxaziridinium zwitterions wherein $R^{34}$ is selected from the group consisting of linear or branched $C_1$–$C_{14}$ substituted or unsubstituted alkyl, or oxaziridinium zwitterions wherein $R^{34}$ is a radical represented by the formula:

wherein $Z^-$ is $-CO_2^-$, $-SO_3^-$ or $-OSO_3^-$, a is 1 and $T_o$ is selected from the group consisting of:

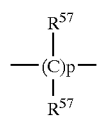

wherein p is an integer from 2 to 4, and $R^{57}$ is independently selected from the group consisting of H and linear or branched $C_1$–$C_{18}$ substituted or unsubstituted alkyl; (2) oxaziridinium polyions having a net negative charge wherein $R^{33}$ is H and $R^{34}$ is selected from the group consisting of a radical represented by the formula:

wherein $Z^-$ is —$CO_2^-$, —$SO_3^-$ or —$OSO_3^-$, a is 1 and $T_o$ is selected from the group consisting of:

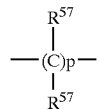

wherein p is an integer from 2 to 4, and $R^{57}$ is independently selected from the group consisting of H and linear or branched $C_1$–$C_{18}$ substituted or unsubstituted alkyl; and (3) oxaziridinium polyions having a net negative charge wherein $R^{33}$ is H, Z is —$CO_2^-$, —$SO_3^-$ or —$OSO_3^-$ and a is 2.

In accordance with another aspect of the present invention, cationic or zwitterionic laundry bleach boosting compounds are provided. Such bleach boosting compounds are preferably selected from the group consisting of:

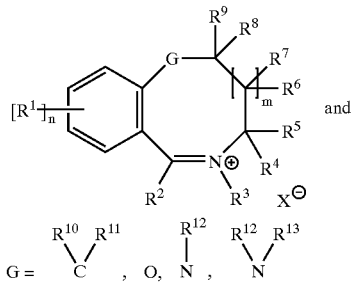
[I]

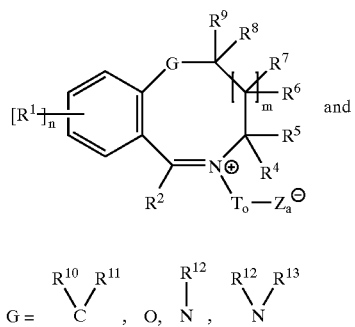
[II]

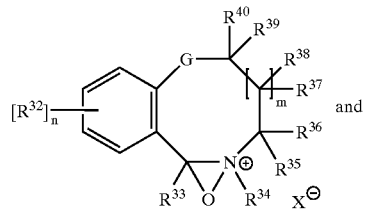
[III]

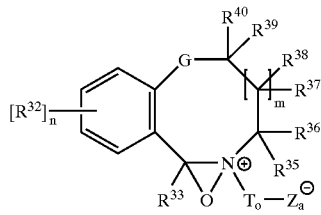
[IV]

and mixtures thereof, wherein $R^{32}$–$R^{44}$ are the same as $R^1$–$R^{13}$, respectively, wherein: m is 0 or 1 and n is an integer from 0 to 4; $R^1$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^1$ substituents may combine to form a fused aryl, fused carbocyclic or fused heterocyclic ring; $R^2$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^3$ may be a substituted or unsubstituted, saturated or unsaturated, radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of —$CO_2^-$, —$SO_3^-$, —$OSO_3^-$, —$SO_2^-$ and —$OSO_2^-$ and a is either 1 or 2; $T_o$ is selected from the group consisting of: (1) —(CH($R^{14}$))— or —(C($R^{14}$)$_2$)— wherein $R^{14}$ is independently selected from H or $C_1$–$C_8$ alkyl; (2) —$CH_2(C_6H_4)$—;

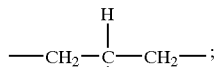
(3)

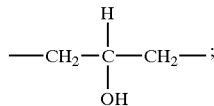
(4)

(5) —(CH$_2$)$_d$(E)(CH$_2$)$_f$— wherein d is from 2 to 8, f is from 1 to 3 and E is —C(O)O—;
(6) —C(O)NR$^{15}$— wherein R$^{15}$ is H or C$_1$–C$_4$ alkyl;

(7)

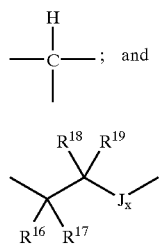

(8)

wherein x is equal to 0–3; J, when present, is independently selected from the group consisting of —CR$^{20}$R$^{21}$—, —CR$^{20}$R$^{21}$CR$^{22}$R$^{23}$—, and —CR$^{20}$R$^{21}$CR$^{22}$R$^{23}$CR$^{24}$R$^{25}$—; R$^{16}$–R$^{25}$ are substituted or unsubstituted radicals selected the linear or branched group consisting of H, C$_1$–C$_{18}$ alkyls, cycloalkyls, alkaryls, aryls, aralkyls, alkylenes, heterocyclic rings, alkoxys, arylcarbonyls, carboxyalkyls and amide groups; R$^4$–R$^{11}$ are substituted or unsubstituted radicals independently selected from the group consisting of H, linear or branched C$_1$–C$_{12}$ alkyls, alkylenes, alkoxys, aryls, alkaryls, aralkyls, cycloalkyls, and heterocyclic rings, and R$^{12}$ and R$^{13}$ are substituted or unsubstituted radicals independently selected from the group consisting of H, oxygen, linear or branched C$_1$–C$_{12}$ alkyls, alkylenes, alkoxys, aryls, alkaryls, aralkyls, cycloalkyls, and heterocyclic rings;

provided that in the case of formula [I], any of R$^1$–R$^{13}$ may be joined together with any other of R$^1$–R$^{13}$ to form part of a common ring; any geminal R$^4$–R$^{11}$ may combine to form a carbonyl; any vicinal R$^4$–R$^{13}$ may join to form unsaturation; and wherein any one group of substituents R$^4$–R$^7$, R$^6$–R$^9$, or R$^8$–R$^{13}$ may combine to form a substituted or unsubstituted fused unsaturated moiety; provided that when G=NR$^{12}$ or G=NR$^{12}$R$^{13}$, then R$^1$ or R$^2$ is not an aryl radical, and when G=CR$^{10}$R$^{11}$ or G=O, then the net charge on R$^3$ is not 0; and provided that, in the case of formula [II], any of R$^{32}$–R$^{44}$ may be joined together with any other of R$^{32}$–R$^{44}$ to form part of a common ring; any geminal R$^{35}$–R$^{44}$ may combine to form a carbonyl, any vicinal R$^{35}$–R$^{44}$ may join to form unsaturation; and wherein any one group of substituents R$^{35}$–R$^{38}$, R$^{37}$–R$^{40}$, R$^{39}$–R$^{44}$, when present, may combine to form a substituted or unsubstituted fused unsaturated moiety.

In another embodiment of the present invention, a method for laundering a fabric in need of laundering is provided. The preferred method comprises contacting the fabric with a laundry solution. The fabric may comprise most any fabric capable of being laundered in normal consumer use conditions. The laundry solution comprises a bleaching composition, as fully described herein. The water temperatures preferably range from about 0° C. to about 50° C. or higher. The water to fabric ratio is preferably from about 1:1 to about 15:1.

The laundry solution may further include at least one additional ingredient selected from the group consisting of detersive surfactants, chelating agents, detersive enzymes and mixtures thereof. Preferably, the laundry solution has a pH of about 6 to about 12, more preferably from about 8 to about 10.5 in a 1% solution of the bleaching composition.

In accordance with another aspect of the present invention, a laundry additive product is provided. The laundry additive product comprises a bleach boosting compound, as fully described above. Such a laundry additive product would be ideally suited for inclusion in a wash process when additional bleaching effectiveness is desired. Such instances may include, but are not limited to, low-temperature solution laundry application.

It is desirable that the laundry additive product further includes a peroxygen source, as fully described above. The laundry additive product can also include powdered or liquid compositions containing a hydrogen peroxide source or a peroxygen source as fully defined above.

Furthermore, if the laundry additive product includes a hydrogen peroxide source, it is desirable that the laundry additive product further includes a bleach activator, as fully described above.

Preferably, the laundry additive product is packaged in dosage form for addition to a laundry process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of composition if desired. Suitable filler or carrier materials may be selected from but not limited to various salts of sulfate, carbonate and silicate as well as talc, clay and the like. Filler or carrier materials for liquid compositions may be water or low molecular weight primary and secondary alcohols including polyols and diols. Examples include methanol, ethanol, propanol and isopropanol. Monohydric alcohols may also be employed. The compositions may contain from about 5% to about 90% of such materials. Acidic fillers can be used to reduce pH.

When the bleach boosting compounds of the present invention are other than an aryliminium zwitterion or oxaziridinium zwitterion, a suitable bleach compatible, charge-balancing counterion is also present.

Bleaching Compositions Comprising Bleach Boosting Compounds

In addition to the use of bleach boosting compounds discussed above, the bleach boosting compounds of the present invention may be employed in conjunction with or without, preferably with a peroxygen source in other bleaching compositions, regardless of their form. For example, the bleach boosting compounds may be employed in a laundry additive product.

In the bleaching compositions of the present invention, the peroxygen source may be present in levels of from about 0.1% (1 ppm) to about 60% (600 ppm) by weight of the composition, and preferably from about 1% (10 ppm) to about 40% (400 ppm) by weight of the composition, and the bleach boosting compound and/or bleaching species may be present from about 0.00001% (0.0001 ppm) to about 10% (100 ppm) by weight of the composition, and preferably from about 0.0001% (0.001 ppm) to about 2% (20 ppm) by weight of the composition, more preferably from about 0.005% (0.05 ppm) to about 0.5% (5 ppm), even more preferably from about 0.01% (0.1 ppm) to about 0.2% (2 ppm). Most preferably from about 0.02% (0.2 ppm) to about 0.1% (1 ppm).

Preferably, the bleaching compositions of the present invention bleach composition comprise an amount of bleach boosting compound and/or bleaching species such that the resulting concentration of the bleach boosting compound in a wash solution is from about 0.001 ppm to about 5 ppm.

Further, preferably the bleach compositions of the present invention comprise an amount of peroxygen compound, when present, and an amount of bleach boosting compound and/or bleaching species, such that the resulting molar ratio of said peroxygen compound to bleach boosting compound and/or bleaching species in a wash solution is preferably greater than 1:1, more preferably greater than 10:1, even more preferably greater than 50:1. The preferred molar ratio ranges of peroxygen compound to bleach boosting compound range from about 30,000:1 to about 10:1, even more preferably from about 10,000:1 to about 50:1, yet even more preferably from about 5,000:1 to about 100:1, still even more preferably from about 3,500:1 to about 150:1.

The conversion values (in ppm) are provided for exemplary purposes, based on an in-use product concentration of 1000 ppm. A 1000 ppm wash solution of a product containing 0.2% booster by weight results in a booster concentration of 2 ppm. Similarly, a 3500 ppm wash solution of a product containing 0.2% booster by weight results in a booster concentration of 6.5 ppm.

The method for delivering bleach boosting compounds of the present invention and the method for delivering bleaching compositions (products) containing such bleach boosting compounds that are particularly useful in the methods of the present invention are the bleach boosting compounds and compositions containing same that satisfy the preferred method for bleaching a stained substrate in an aqueous medium with a peroxygen source and with an bleach boosting compound whose structures is defined herein and wherein said medium contains active oxygen from the peroxygen compound from about 0.05 to about 250 ppm per liter of medium, and said bleach boosting compound from 0.001 ppm to about 5 ppm, preferably from about 0.01 ppm to about 3 ppm, more preferably from about 0.1 ppm to about 2 ppm, and most preferably from about 0.2 ppm to about 1 ppm.

Such a preferred method for bleaching a stained substrate in an aqueous medium with a peroxygen source and with an bleach boosting compound is of particular value for those applications in which the color safety of the stained substrate in need of cleaning is a concern. In such applications the preferred embodiment (e.g., 0.01 ppm to about 3 ppm) is of particular importance in terms of achieving acceptable fabric color safety. For other applications in which color safety of the stained substrate in need of cleaning is of less concern, a higher in-use concentration may be preferred.

The bleaching compositions of the present invention may be advantageously employed in laundry applications including, but not limited to, stain bleaching, dye transfer inhibition, and whitening, hard surface cleaning, automatic dishwashing applications, as well as cosmetic applications such as dentures, teeth, hair and skin. However, due to the unique advantages of both increased effectiveness in lower temperature solutions and the superior bleaching effectiveness, the bleach boosters of the present invention are ideally suited for laundry applications such as the bleaching of fabrics through the use of bleach containing detergents or laundry bleach additives. Furthermore, the bleach boosting compounds of the present invention may be employed in both granular and liquid compositions.

The bleach boosting compounds and bleaching composition comprising the bleach boosting compounds can be used as antimicrobial agents and disinfectants.

Accordingly, the bleaching compositions of the present invention may include various additional ingredients which are desirable in laundry applications. Such ingredients include detersive surfactants, bleach catalysts, builders, chelating agents, enzymes, polymeric soil release agents, brighteners and various other ingredients. Compositions including any of these various additional ingredients preferably have a pH of from about 6 to about 12, more preferably from about 8 to about 10.5 in a 1% solution of the bleaching composition.

The bleaching compositions preferably include at least one detersive surfactant, at least one chelating agent, at least one detersive enzyme and preferably has a pH of about 6 to about 12, more preferably from about 8 to about 10.5 in a 1% solution of the bleaching composition. Also preferably, at least one detersive surfactant contained in the bleaching composition is an anionic surfactant.

In another embodiment of the present invention, a method for laundering a fabric in need of laundering is provided. The preferred method comprises contacting the fabric with a laundry solution. The fabric may comprise most any fabric capable of being laundered in normal consumer use conditions. The laundry solution comprises a bleaching composition, as fully described herein. The water temperatures preferably range from about 0° C. to about 50° C. or higher. The water to fabric ratio is preferably from about 1:1 to about 15:1.

The laundry solution may further include at least one additional ingredient selected from the group consisting of detersive surfactants, chelating agents, detersive enzymes and mixtures thereof. Preferably, the laundry solution has a pH of about 6 to about 12, more preferably from about 8 to about 10.5 in a 1% solution of the bleaching composition.

In accordance with another aspect of the present invention, a laundry additive product is provided. The laundry additive product comprises an bleach boosting compound, as fully described above. Such a laundry additive product would be ideally suited for inclusion in a wash process when additional bleaching effectiveness is desired. Such instances may include, but are not limited to, low-temperature and medium temperature solution laundry application.

It is desirable that the laundry additive product further includes a peroxygen source, as fully described above. The laundry additive product can also include powdered or liquid compositions containing a hydrogen peroxide source or a peroxygen source as fully defined above.

Furthermore, if the laundry additive product includes a hydrogen peroxide source, it is desirable that the laundry additive product further includes a bleach activator, as fully described above.

Preferably, the laundry additive product is packaged in dosage form for addition to a laundry process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of composition if desired. Suitable filler or carrier materials may be selected from but not limited to various salts of sulfate, carbonate and silicate as well as talc, clay and the like. Filler or carrier materials for liquid compositions may be water or low molecular weight primary and secondary alcohols including polyols and diols. Examples include methanol, ethanol, propanol and isopropanol. Monohydric alcohols may also be employed. The compositions may contain from about 5% to about 90% of such materials. Acidic fillers can be used to reduce pH.

A preferred bleaching composition is a bleaching composition comprising:
(a) a peroxygen source; and
(b) an bleach boosting compounds;
wherein the bleach boosting compounds becomes active in a wash solution containing said bleaching composition a period of time after said peroxygen source becomes active.

The peroxygen source, like discussed above, is preferably selected from the group consisting of:

(i) preformed peracid compounds selected from the group consisting of percarboxylic acids and salts, percarbonic acids and salts, perimidic acids and salts, peroxymonosulfuric acids and salts, and mixtures thereof, and (ii) hydrogen peroxide sources selected from the group consisting of perborate compounds, percarbonate compounds, perphosphate compounds and mixtures thereof, and a bleach activator.

Bleaching System—In addition to the bleach boosting of the present invention, the bleaching compositions of the present invention preferably comprise a bleaching system. Bleaching systems typically comprise a peroxygen source. Peroxygen sources are well-known in the art and the peroxygen source employed in the present invention may comprise any of these well known sources, including peroxygen compounds as well as compounds which under consumer use conditions provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention. Preferably, the peroxygen source is selected from the group consisting of:

(i) preformed peracid compounds selected from the group consisting of percarboxylic acids and salts, percarbonic acids and salts, perimidic acids and salts, peroxymonosulfuric acids and salts, and mixtures thereof, and (ii) hydrogen peroxide sources selected from the group consisting of perborate compounds, percarbonate compounds, perphosphate compounds and mixtures thereof, and a bleach activator.

When present, peroxygen sources (peracids and/or hydrogen peroxide sources) will typically be at levels of from about 1%, preferably from about 5% to about 30%, preferably to about 20% by weight of the composition. If present, the amount of bleach activator will typically be from about 0.1%, preferably from about 0.5% to about 60%, preferably to about 40% by weight, of the bleaching composition comprising the bleaching agent-plus-bleach activator.

a. Preformed Peracids—The preformed peracid compound as used herein is any convenient compound which is stable and which under consumer use conditions provides an effective amount of peracid anion. The bleach boosters of the present invention may of course be used in conjunction with a preformed peracid compound selected from the group consisting of percarboxylic acids and salts, percarbonic acids and salts, perimidic acids and salts, peroxymonosulfuric acids and salts, and mixtures thereof, examples of which are described in U.S. Pat. No. 5,576,282 to Miracle et al.

One class of suitable organic peroxycarboxylic acids have the general formula:

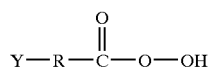

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

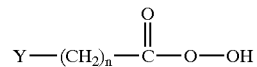

where Y can be, for example, H, $CH_3$, $CH_2Cl$, $C(O)OH$, or $C(O)OOH$; and n is an integer from 0 to 20. When the organic peroxycarboxylic acid is aromatic, the unsubstituted peracid has the general formula:

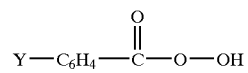

wherein Y can be, for example, hydrogen, alkyl, alkylhalogen, halogen, C(O)OH or C(O)OOH.

Typical monoperoxy acids useful herein include alkyl and aryl peroxyacids such as:

(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);

(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);

(iii) amidoperoxyacids, e.g. mononoylamide of either peroxysuccinic acid (NAPSA) or of peroxyadipic acid (NAPAA).

Typical diperoxyacids useful herein include alkyl diperoxyacids and aryldiperoxyacids, such as:

(iv) 1,12-diperoxydodecanedioic acid;

(v) 1,9-diperoxyazelaic acid;

(vi) diperoxybrassylic acid; diperoxysebacic acid and diperoxyisophthalic acid;

(vii) 2-decyldiperoxybutane-1,4-dioic acid;

(viii) 4,4'-sulfonylbisperoxybenzoic acid.

Such bleaching agents are disclosed in U.S. Pat. No. 4,483,781, Hartman, issued Nov. 20, 1984, U.S. Pat. No. 4,634,551 to Burns et al., European Patent Application 0,133,354, Banks et al. published Feb. 20, 1985, and U.S. Pat. No. 4,412,934, Chung et al. issued Nov. 1, 1983. Sources also include 6-nonylamino-6-oxoperoxycaproic acid as fully described in U.S. Pat. No. 4,634,551, issued Jan. 6, 1987 to Burns et al. Persulfate compounds such as for example OXONE, manufactured commercially by E.I. DuPont de Nemours of Wilmington, Del. can also be employed as a suitable source of peroxymonosulfuric acid.

b. Hydrogen Peroxide Sources—The hydrogen peroxide source may be any suitable hydrogen peroxide source and present at such levels as fully described in U.S. Pat. No. 5,576,282. For example, the hydrogen peroxide source may be selected from the group consisting of perborate compounds, percarbonate compounds, perphosphate compounds and mixtures thereof.

Hydrogen peroxide sources are described in detail in the herein incorporated Kirk Othmer's Encyclopedia of Chemical Technology, 4th Ed (1992, John Wiley & Sons), Vol. 4, pp. 271–300 "Bleaching Agents (Survey)", and include the various forms of sodium perborate and sodium percarbonate, including various coated and modified forms.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

Compositions of the present invention may also comprise as the bleaching agent a chlorine-type bleaching material. Such agents are well known in the art, and include for example sodium dichloroisocyanurate ("NaDCC"). However, chlorine-type bleaches are less preferred for compositions which comprise enzymes.

c. Bleach Activators—Preferably, the peroxygen source in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which when used in conjunction with a hydrogen peroxide source leads to the in situ production of the peracid corresponding to the bleach activator. Various non limiting examples of activators are fully disclosed in U.S. Pat. No. 5,576,282, U.S. Pat. No. 4,915,854 and U.S. Pat. No. 4,412,934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group.

Preferred hydrophobic bleach activators include, but are not limited to, nonanoyloxybenzenesulphonate (NOBS), 4-[N-(nonanoyl) amino hexanoyloxy]-benzene sulfonate sodium salt (NACA-OBS) an example of which is described in U.S. Pat. No. 5,523,434, lauroyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA).

Preferred bleach activators are those described in U.S. Pat. No. 5,698,504 Christie et al., issued Dec. 16, 1997; U.S. Pat. No. 5,695,679 Christie et al. issued Dec. 9, 1997; U.S. Pat. No. 5,686,401 Willey et al., issued Nov. 11, 1997; U.S. Pat. No. 5,686,014 Hartshorn et al., issued Nov. 11, 1997; U.S. Pat. No. 5,405,412 Willey et al., issued Apr. 11, 1995; U.S. Pat. No. 5,405,413 Willey et al., issued Apr. 11, 1995; U.S. Pat. No. 5,130,045 Mitchel et al., issued Jul. 14, 1992; and U.S. Pat. No. 4,412,934 Chung et al., issued Nov. 1, 1983, and copending patent applications U.S. Ser. Nos. 08/709,072, 08/064,564, all of which are incorporated herein by reference.

The mole ratio of peroxygen bleaching compound (as AvO) to bleach activator in the present invention generally ranges from at least 1:1, preferably from about 20:1, more preferably from about 10:1 to about 1:1, preferably to about 3:1.

Quaternary substituted bleach activators may also be included. The present bleaching compositions preferably comprise a quaternary substituted bleach activator (QSBA) or a quaternary substituted peracid (QSP); more preferably, the former. Preferred QSBA structures are further described in U.S. Pat. No. 5,686,015 Willey et al., issued Nov. 11, 1997; U.S. Pat. No. 5,654,421 Taylor et al., issued Aug. 5, 1997; U.S. Pat. No. 5,460,747 Gosselink et al., issued Oct. 24, 1995; U.S. Pat. No. 5,584,888 Miracle et al., issued Dec. 17, 1996; and U.S. Pat. No. 5,578,136 Taylor et al., issued Nov. 26, 1996; all of which are incorporated herein by reference.

Highly preferred bleach activators useful herein are amide-substituted as described in U.S. Pat. No. 5,698,504, U.S. Pat. No. 5,695,679, and U.S. Pat. No. 5,686,014 each of which are cited herein above. Preferred examples of such bleach activators include: (6-octanamidocaproyl) oxybenzenesulfonate, (6-nonanamidocaproyl) oxybenzenesulfonate, (6-decanamido caproyl) oxybenzenesulfonate and mixtures thereof.

Other useful activators, disclosed in U.S. Pat. No. 5,698,504, U.S. Pat. No. 5,695,679, U.S. Pat. No. 5,686,014 each of which is cited herein above and U.S. Pat. No. 4,966,723 Hodge et al., issued Oct. 30, 1990, include benzoxazin-type activators, such as a $C_6H_4$ ring to which is fused in the 1,2-positions a moiety —C(O)OC($R^1$)=N—.

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. No. 5,698,504, U.S. Pat. No. 5,695,679 and U.S. Pat. No. 5,686,014, each of which is cited herein above, are very useful herein, especially the acyl caprolactams (see for example WO 94-28102 A) and acyl valerolactams (see U.S. Pat. No. 5,503,639 Willey et al., issued Apr. 2, 1996 incorporated herein by reference).

d. Organic Peroxides, especially Diacyl Peroxides—In addition to the bleaching agents described above, the bleaching compositions of the present invention can optionally include organic peroxides. Organic peroxidase are extensively illustrated in Kirk Othmer, Encyclopedia of Chemical Technology, Vol. 17, John Wiley and Sons, 1982 at pages 27–90 and especially at pages 63–72, all incorporated herein by reference. If a diacyl peroxide is used, it will preferably be one which exerts minimal adverse impact on spotting/filming.

e. Metal-containing Bleach Catalysts—The bleaching compositions can also optionally include metal-containing bleach catalysts, preferably manganese and cobalt-containing bleach catalysts.

One type of metal-containing bleach catalyst is a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 Bragg, issued Feb. 2, 1982.

i. Manganese Metal Complexes—If desired, the compositions herein can be catalyzed by means of a manganese compound. Such compounds and levels of use are well known in the art and include, for example, the manganese-based catalysts disclosed in U.S. Pat. No. 5,576,282 Miracle et al., issued Nov. 19, 1996; U.S. Pat. No. 5,246,621 Favre et al., issued Sep. 21, 1993; U.S. Pat. No. 5,244,594 Favre et al., issued Sep. 14, 1993; U.S. Pat. No. 5,194,416 Jureller et al., issued Mar. 16, 1993; U.S. Pat. No. 5,114,606 van Vliet et al., issued May 19, 1992; and European Pat. App. Pub. Nos. 549,271 A1, 549,272 A1, 544,440 A2, and 544, 490 A1; Preferred examples of these catalysts include $Mn^{IV}_2$ $(u-O)_3(1,4,7$-trimethyl-1,4,7-triazacyclononane$)_2$-$(PF_6)_2$, $Mn^{III}_2(u-O)_1$ $(u-OAc)_2(1,4,7$-trimethyl-1,4,7-triazacyclononane$)_2(ClO_4)_2$, $Mn^{IV}_4(u-O)_6(1,4,7$-triazacyclononane$)_4(ClO_4)_4$, $Mn^{III}Mn^{IV}_4(u-O)_1(u-OAc)_2$-$(1,4,7$-trimethyl-1,4,7-triazacyclononane$)_2(ClO_4)_3$, $Mn^{IV}(1,4,7$-trimethyl-1,4,7-triazacyclononane)-$(OCH_3)_3(PF_6)$, and mixtures thereof. Other metal-based bleach catalysts include those disclosed in U.S. Pat. No. 4,430,243 included by reference herein above and U.S. Pat. No. 5,114,611 van Kralingen, issued May 19, 1992. The use of manganese with various complex ligands to enhance bleaching is also reported in the following: U.S. Pat. No. 4,728,455 Rerek, issued Mar. 1, 1988; U.S. Pat. No. 5,284,944 Madison, issued Feb. 8, 1994; U.S. Pat. No. 5,246,612 van Dijk et al., issued Sep. 21, 1993; U.S. Pat. No. 5,256,779 Kerschner et al., issued Oct. 26, 2993; U.S. Pat. No. 5,280,117 Kerschner et al., issued Jan. 18, 1994; U.S. Pat. No. 5,274,147 Kerschner et al., issued Dec. 28, 1993; U.S. Pat. No. 5,153,161 Kerschner et al., issued Oct. 6, 1992; and U.S. Pat. No. 5,227,084 Martens et al., issued Jul. 13, 1993.

ii. Cobalt Metal Complexes—Cobalt bleach catalysts useful herein are known, and are described, for example, in U.S. Pat. No. 5,597,936 Perkins et al., issued Jan. 28, 1997; U.S. Pat. No. 5,595,967 Miracle et al., Jan. 21, 1997; U.S. Pat. No. 5,703,030 Perkins et al., issued Dec. 30, 1997; and M. L. To be, "Base Hydrolysis of Transition-Metal Complexes", *Adv. Inorg. Bioinorg. Mech.*, (1983), 2, pages 1–94. The most preferred cobalt catalyst useful herein are cobalt pentaamine acetate salts having the formula [Co(NH$_3$)$_5$OAc]T$_y$, wherein "OAc" represents an acetate moiety and "T$_y$" is an anion, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co(NH$_3$)$_5$OAc](BF$_4$)$_2$; and [Co(NH$_3$)$_5$OAc](NO$_3$)$_2$ (herein "PAC").

These cobalt catalysts are readily prepared by known procedures, such as taught for example in U.S. Pat. No. 5,597,936, U.S. Pat. No. 5,595,967, U.S. Pat. No. 5,703,030, cited herein above, the To be article and the references cited therein, and in U.S. Pat. No. 4,810,410, to Diakun et al, issued Mar. 7, 1989, *J. Chem. Ed.* (1989), 66 (12), 1043–45; The Synthesis and Characterization of Inorganic Compounds, W. L. Jolly (Prentice-Hall; 1970), pp. 461–3; *Inorg. Chem.*, 18, 1497–1502 (1979); *Inorg. Chem.*, 21, 2881–2885 (1982); *Inorg. Chem.*, 18, 2023–2025 (1979); Inorg. Synthesis, 173–176 (1960); and *Journal of Physical Chemistry*, 56,22–25 (1952).

iii. Transition Metal Complexes of Macropolycyclic Rigid Ligands—Compositions herein may also suitably include as bleach catalyst a transition metal complex of a macropolycyclic rigid ligand. The phrase "macropolycyclic rigid ligand" is sometimes abbreviated as "MRL" in discussion below. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Suitable transition metals e.g., Mn are illustrated hereinafter. "Macropolycyclic" means a MRL is both a macrocycle and is polycyclic. "Polycyclic" means at least bicyclic. The term "rigid" as used herein herein includes "having a superstructure" and "cross-bridged". "Rigid" has been defined as the constrained converse of flexibility: see D. H. Busch., *Chemical Reviews.*, (1993), 93, 847–860, incorporated by reference. More particularly, "rigid" as used herein means that the MRL must be determinably more rigid than a macrocycle ("parent macrocycle") which is otherwise identical (having the same ring size and type and number of atoms in the main ring) but lacking a superstructure (especially linking moieties or, preferably cross-bridging moieties) found in the MRL's. In determining the comparative rigidity of macrocycles with and without superstructures, the practitioner will use the free form (not the metal-bound form) of the macrocycles. Rigidity is well-known to be useful in comparing macrocycles; suitable tools for determining, measuring or comparing rigidity include computational methods (see, for example, Zimmer, *Chemical Reviews.* (1995), 95(38), 2629–2648 or Hancock et al., *Inorganica Chimica Acta*, (1989), 164, 73–84.

Preferred MRL's herein are a special type of ultra-rigid ligand which is cross-bridged. A "cross-bridge" is nonlimitingly illustrated in 1.11 hereinbelow. In 1.11, the cross-bridge is a —$CH_2CH_2$— moiety. It bridges $N^1$ and $N^8$ in the illustrative structure. By comparison, a "same-side" bridge, for example if one were to be introduced across $N^1$ and $N^{12}$ in 1.11, would not be sufficient to constitute a "cross-bridge" and accordingly would not be preferred.

Suitable metals in the rigid ligand complexes include Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV). Preferred transition-metals in the instant transition-metal bleach catalyst include manganese, iron and chromium.

More generally, the MRL's (and the corresponding transition-metal catalysts) herein suitably comprise:

(a) at least one macrocycle main ring comprising four or more heteroatoms; and
(b) a covalently connected non-metal superstructure capable of increasing the rigidity of the macrocycle, preferably selected from
 (i) a bridging superstructure, such as a linking moiety;
 (ii) a cross-bridging superstructure, such as a cross-bridging linking moiety; and
 (iii) combinations thereof.

The term "superstructure" is used herein as defined in the literature by Busch et al., see, for example, articles by Busch in "Chemical Reviews".

Preferred superstructures herein not only enhance the rigidity of the parent macrocycle, but also favor folding of the macrocycle so that it coordinates to a metal in a cleft. Suitable superstructures can be remarkably simple, for example a linking moiety such as any of those illustrated in FIG. 1 and FIG. 2 below, can be used.

FIG. 1 wherein n is an integer, for example from 2 to 8, preferably less than 6, typically 2 to 4, or

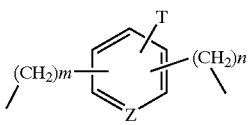

FIG. 2 wherein m and n are integers from about 1 to 8, more preferably from 1 to 3; Z is N or CH; and T is a compatible substituent, for example H, alkyl, trialkylammonium, halogen, nitro, sulfonate, or the like. The aromatic ring in 1.10 can be replaced by a saturated ring, in which the atom in Z connecting into the ring can contain N, O, S or C.

Suitable MRL's are further nonlimitingly illustrated by the following compound:

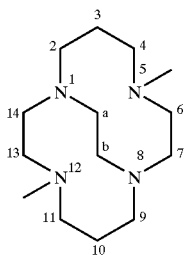

FIG. 3

This is a MRL in accordance with the invention which is a highly preferred, cross-bridged, methyl-substituted (all nitrogen atoms tertiary) derivative of cyclam. Formally, this ligand is named 5,12-dimethyl-1,5,8,12-tetraazabicyclo [6.6.2]hexadecane using the extended von Baeyer system. See "A Guide to IUPAC Nomenclature of Organic Compounds: Recommendations 1993", R. Panico, W. H. Powell and J-C Richer (Eds.), Blackwell Scientific Publications, Boston, 1993; see especially section R-2.4.2.1.

Transition-metal bleach catalysts of Macrocyclic Rigid Ligands which are suitable for use in the invention compositions can in general include known compounds where they conform with the definition herein, as well as, more preferably, any of a large number of novel compounds expressly designed for the present laundry or cleaning uses, and non-limitingly illustrated by any of the following:

Dichloro-5,12-dimethyl-1,5,8,12-tetraazabicyclo[6.6.2] hexadecane Manganese(II)
Diaquo-5,12-dimethyl-1,5,8,12-tetraazabicyclo[6.6.2] hexadecane Manganese(II) Hexafluorophosphate
Aquo-hydroxy-5,12-dimethyl-1,5,8,12-tetraazabicyclo [6.6.2]hexadecane Manganese(III) Hexafluorophosphate
Diaquo-5,12-dimethyl-1,5,8,12-tetraazabicyclo[6.6.2] hexadecane Manganese(II) Tetrafluoroborate
Dichloro-5,12-dimethyl-1,5,8,12-tetraazabicyclo[6.6.2] hexadecane Manganese(III) Hexafluorophosphate
Dichloro-5,12-di-n-butyl-1,5,8,12-tetraaza bicyclo[6.6.2] hexadecane Manganese(II)
Dichloro-5,12-dibenzyl-1,5,8,12-tetraazabicyclo[6.6.2] hexadecane Manganese(II)
Dichloro-5-n-butyl-12-methyl-1,5,8,12-tetraaza-bicyclo [6.6.2]hexadecane Manganese(II)
Dichloro-5-n-octyl-12-methyl-1,5,8,12-tetraaza-bicyclo [6.6.2]hexadecane Manganese(II)
Dichloro-5-n-butyl-12-methyl-1,5,8,12-tetraaza-bicyclo [6.6.2]hexadecane Manganese(II).

(f) Other Bleach Catalysts—The compositions herein may comprise one or more other bleach catalysts. Preferred bleach catalysts are zwitterionic bleach catalysts, which are described in U.S. Pat. No. 5,576,282 (especially 3-(3,4-dihydroisoquinolinium) propane sulfonate. Other bleach catalysts include cationic bleach catalysts are described in U.S. Pat. Nos. 5,360,569, 5,442,066, 5,478,357, 5,370,826, 5,482,515, 5,550,256, and WO 95/13351, WO 95/13352, and WO 95/13353.

As a practical matter, and not by way of limitation, the compositions and cleaning processes herein can be adjusted to provide on the order of at least one part per hundred million of the active bleach catalyst species in the aqueous washing medium, and will preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic washing process, typical compositions herein will comprise from about 0.0005% to about 0.2%, more preferably from about 0.004% to about 0.08%, of bleach catalyst, especially manganese or cobalt catalysts, by weight of the cleaning compositions.

Preferably, the peroxygen source is selected from hydrogen peroxide sources selected from the group consisting of perborate compounds, percarbonate compounds, perphosphate compounds and mixtures thereof, and a bleach activator.

Preferably, the bleach activator is selected from the group consisting of hydrophobic bleach activators as disclosed herein.

The purpose of such a bleaching composition is to mitigate unwanted decomposition of the bleach boosting, and to allow the peracid to achieve bleaching performance on a fabric in need of cleaning, such as a stained fabric, in a wash solution prior to the availability of the bleach boosting.

The period of time between the peracid becoming active in a wash solution and the bleach boosting compounds becoming active can be in the range of from about 1 second to about 24 hours. Alternatively, since the bleach boosting compounds are relatively stable in the wash solution, the peracid can become active in the wash solution after the bleach boosting compound becomes active or available.

The purpose of a delayed addition bleaching composition (which may or may not be used in conjunction with this invention) is to allow the peracid to achieve maximum bleaching performance on a fabric in need of cleaning, such as a stained fabric, in a wash solution prior to the introduction of the bleach boosting compound. In other words, a bleaching composition comprising a bleach boosting compound which becomes active in a wash solution after a fabric in need of cleaning has been added to the wash solution. Methods for delayed (controlled) addition of bleach boosting compounds are more fully described in copending and co-owned U.S. Provisional Patent Application Ser. No. 60/151,002 entitled "Controlled Availability of Formulation Components, Compositions and Laundry Methods Employing Same" filed Aug. 27, 1999.

Alternatively, since the bleach boosting compounds can have increased stability, a bleaching composition comprising an bleach boosting compound which becomes active in a wash solution prior to a fabric in need of cleaning has been added to the wash solution may be used.

The bleaching compositions of the present invention also comprise, in addition to one or more bleach boosters, described hereinbefore, one or more cleaning adjunct materials, preferably compatible with the bleach boosting(s) and/or any enzymes present in the bleaching composition. The term "compatible", as used herein, means the bleaching composition materials do not reduce the bleaching activity of the bleach boosting and/or any enzymatic activity of any enzyme present in the bleaching composition to such an extent that the bleach boosting and/or enzyme is not effective as desired during normal use situations. The term "cleaning adjunct materials", as used herein, means any liquid, solid or gaseous material selected for the particular type of bleaching composition desired and the form of the product (e.g., liquid; granule; powder; bar; paste; spray; tablet; gel; foam composition), which materials are also preferably compatible with the protease enzyme(s) and bleaching agent(s) used in the composition. Granular compositions can also be in "compact" form and the liquid compositions can also be in a "concentrated" form.

The specific selection of cleaning adjunct materials are readily made by considering the surface, item or fabric to be cleaned, and the desired form of the composition for the cleaning conditions during use (e.g., through the wash detergent use). Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments and pH control agents as described in U.S. Pat. Nos. 5,705,464, 5,710,115, 5,698,504, 5,695,679, 5,686,014 and 5,646,101. Specific bleaching composition materials are exemplified in detail hereinafter.

If the cleaning adjunct materials are not compatible with the protease variant(s) in the bleaching compositions, then suitable methods of keeping the cleaning adjunct materials and the protease variant(s) separate (not in contact with each other) until combination of the two components is appropriate can be used. Suitable methods can be any method known in the art, such as gelcaps, encapulation, tablets, physical separation, etc.

Such bleaching compositions include detergent compositions for cleaning hard surfaces, unlimited in form (e.g., liquid, granular, paste, foam, spray, etc.); detergent compositions for cleaning fabrics, unlimited in form (e.g., granular, liquid, bar formulations, etc.); dishwashing compositions (unlimited in form and including both granular and liquid automatic dishwashing); oral bleaching compositions, unlimited in form (e.g., dentifrice, toothpaste and mouthwash formulations); and denture bleaching compositions, unlimited in form (e.g., liquid, tablet).

The fabric bleaching compositions of the present invention are mainly intended to be used in the wash cycle of a washing machine; however, other uses can be contemplated, such as pretreatment product for heavily-soiled fabrics, or soaking product; the use is not necessarily limited to the washing-machine context, and the compositions of the present invention can be used alone or in combination with compatible handwash compositions.

The bleaching compositions may include from about 1% to about 99.9% by weight of the composition of the cleaning adjunct materials.

As used herein, "non-fabric bleaching compositions" include hard surface bleaching compositions, dishwashing compositions, oral bleaching compositions, denture bleaching compositions and personal cleansing compositions.

When the bleaching compositions of the present invention are formulated as compositions suitable for use in a laundry machine washing method, the compositions of the present invention preferably contain both a surfactant and a builder compound and additionally one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional cleaning adjunct materials.

The compositions of the present invention can also be used as detergent additive products in solid or liquid form. Such additive products are intended to supplement or boost the performance of conventional detergent compositions and can be added at any stage of the cleaning process.

When formulated as compositions for use in manual dishwashing methods the compositions of the invention preferably contain a surfactant and preferably other cleaning adjunct materials selected from organic polymeric compounds, suds enhancing agents, group II metal ions, solvents, hydrotropes and additional enzymes.

If needed the density of the laundry detergent compositions herein ranges from 400 to 1200 g/liter, preferably 500 to 950 g/liter of composition measured at 20° C.

The "compact" form of the bleaching compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulfates and chlorides. A preferred filler salt is sodium sulfate.

Liquid bleaching compositions according to the present invention can also be in a "concentrated form", in such case, the liquid bleaching compositions according the present invention will contain a lower amount of water, compared to conventional liquid detergents. Typically the water content of the concentrated liquid bleaching composition is preferably less than 40%, more preferably less than 30%, most preferably less than 20% by weight of the bleaching composition.

Cleaning Adjunct Materials

While not essential for the purposes of the present invention, several conventional adjuncts illustrated hereinafter are suitable for use in the instant bleaching compositions and may be desirably incorporated in preferred embodiments of the invention, for example to assist or enhance cleaning performance, for treatment of the substrate to be cleaned, or to modify the aesthetics of the bleaching composition as is the case with perfumes, colorants, dyes or the like. The precise nature of these additional components, and levels of incorporation thereof, will depend on the physical form of the composition and the nature of the cleaning operation for which it is to be used. Unless otherwise indicated, the bleaching compositions of the invention may for example, be formulated as granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

Surfactants—The compositions of the present invention preferably contain a detersive surfactant. The detersive surfactant is typically selected from the group consisting of anionic, nonionics, cationics, ampholytics, zwitterionics, and mixtures thereof. By selecting the type and amount of detersive surfactant, along with other adjunct ingredients disclosed herein, the present detergent compositions can be formulated to be used in the context of laundry cleaning or in other different cleaning applications, particularly including dishwashing. The particular surfactants used can therefore vary widely depending upon the particular end-use envisioned. Suitable surfactants are described below. Examples of suitable nonionic, anionic, cationic amphoteric and zwitterionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

The surfactant is typically present at a level of from about 0.1%, preferably about 1%, more preferably about 5% by weight of the bleaching compositions to about 99.9%, preferably about 80%, more preferably about 35%, most preferably 30% about by weight of the bleaching compositions.

Anionic Surfactants—Anionic surfactants useful in the present invention are preferably selected from the group consisting of, linear alkylbenzene sulfonate, alpha olefin sulfonate, paraffin sulfonates, alkyl ester sulfonates, alkyl sulfates, alkyl alkoxy sulfate, alkyl sulfonates, alkyl alkoxy carboxylate, alkyl alkoxylated sulfates, sarcosinates, taurinates, and mixtures thereof. An effective amount, typically from about 0.5% to about 90%, preferably about 5% to about 60%, more preferably from about 10 to about 30%, by weight of anionic detersive surfactant can be used in the present invention.

Alkyl sulfate surfactants are another type of anionic surfactant of importance for use herein. In addition to providing excellent overall cleaning ability when used in combination with polyhydroxy fatty acid amides (see below), including good grease/oil cleaning over a wide range of temperatures, wash concentrations, and wash times, dissolution of alkyl sulfates can be obtained, as well as improved formulability in liquid detergent formulations are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali (Group IA) metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines, e.g. monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium. Surfactants for use herein can be made from natural or synthetic alcohol feedstocks. Chain lengths represent average hydrocarbon distributions, including branching.

Additionally and preferably, the surfactant may be a midchain branched alkyl sulfate, midchain branched alkyl alkoxylate, or midchain branched alkyl alkoxylate sulfate. These surfactants are further described in No. 60/061,971, Oct. 14, 1997, No. 60/061,975, Oct. 14, 1997, Ser. No. 60/062,086, Oct. 14, 1997, No. 60/061,916, Oct. 14, 1997, No. 60/061,970, Oct. 14, 1997, No. 60/062,407, Oct. 14, 1997. Other suitable mid-chain branched surfactants can be found in U.S. Patent applications Ser. Nos. 60/032,035, 60/031,845, 60/031,916, 60/031,917, 60/031,761, 60/031,762 and 60/031,844. Mixtures of these branched surfactants with conventional linear surfactants are also suitable for use in the present compositions.

Another preferred anionic surfactant are the so-called modified alkyl benzene sulfonate surfactants, or MLAS. Some suitable MLAS surfactants, methods of making them and exemplary compositions are further described in copending U.S. Patent applications Ser. Nos. 60/053,319, 60/053,318, 60/053,321, 60/053,209, 60/053,328, 60/053,186, 60/055,437, 60/105,017 and 60/104,962.

Examples of suitable anionic surfactants are given in "Surface Active Agents and Detergents" (Vol. I and II by Schwartz, Perry and Berch).

Nonionic Detergent Surfactants—Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants include: amine oxides, alkyl ethoxylate, alkanoyl glucose amide, alkyl betaines, sulfobetaine and mixtures thereof.

Amine oxides are semi-polar nonionic surfactants and include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

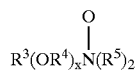

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides. Preferably the amine oxide is present in the composition in an effective amount, more preferably from about 0.1% to about 20%, even more preferably about 0.1% to about 15%, even more preferably still from about 0.5% to about 10%, by weight.

The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal® CO-630, marketed by the GAF Corporation; and Triton® X45, X-114, X-100, and X-102, all marketed by the Rohm & Haas Company. These compounds are commonly referred to as alkyl phenol alkoxylates, (e.g., alkyl phenol ethoxylates).

The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include Tergitol® 15-S-9 (the condensation product of $C_{11}$–$C_{15}$ linear secondary alcohol with 9 moles ethylene oxide), Tergitol® 24-L-6 NMW (the condensation product of $C_{12}$–$C_{14}$ primary alcohol with 6 moles ethylene oxide with a narrow molecular weight distribution), both marketed by Union Carbide Corporation; Neodol® 45-9 (the condensation product of $C_{14}$–$C_{15}$ linear alcohol with 9 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 45-4 (the condensation product of $C_{14}$–$C_{15}$ linear alcohol with 4 moles of ethylene oxide), marketed by Shell Chemical Company, and Kyro® EOB (the condensation product of $C_{13}$–$C_{15}$ alcohol with 9 moles ethylene oxide), marketed by The Procter & Gamble Company. Other commercially available nonionic surfactants include Dobanol 91-8® marketed by Shell Chemical Co. and Genapol UD-080® marketed by Hoechst. This category of nonionic surfactant is referred to generally as "alkyl ethoxylates."

The preferred alkylpolyglycosides have the formula

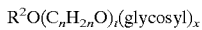

wherein $R^2$ is selected from the group consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Fatty acid amide surfactants having the formula:

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C^2H_4O)_x$H where x varies from about 1 to about 3.

Preferred amides are $C_8$–$C_{20}$ ammonia amides, monoethanolamides, diethanolamides, and isopropanolamides.

Preferably the nonionic surfactant, when present in the composition, is present in an effective amount, more preferably from about 0.1% to about 20%, even more preferably about 0.1% to about 15%, even more preferably still from about 0.5% to about 10%, by weight.

Polyhydroxy Fatty Acid Amide Surfactant—The detergent compositions hereof may also contain an effective amount of polyhydroxy fatty acid amide surfactant. By "effective amount" is meant that the formulator of the composition can select an amount of polyhydroxy fatty acid amide to be incorporated into the compositions that will improve the cleaning performance of the detergent composition. In general, for conventional levels, the incorporation of about 1%, by weight, polyhydroxy fatty acid amide will enhance cleaning performance.

The detergent compositions herein will typically comprise about 1% weight basis, polyhydroxy fatty acid amide surfactant, preferably from about 3% to about 30%, of the polyhydroxy fatty acid amide. The polyhydroxy fatty acid amide surfactant component comprises compounds of the structural formula:

wherein: $R^1$ is H, $C_1$-$C_4$ hydrocarbyl, 2-hydroxy ethyl, 2-hydroxy propyl, or a mixture thereof, preferably $C_1$-$C_4$ alkyl, more preferably $C_1$ or $C_2$ alkyl, most preferably $C_1$ alkyl (i.e., methyl); and $R^2$ is a $C_5$-$C_{31}$ hydrocarbyl, preferably straight chain $C_7$-$C_{19}$ alkyl or alkenyl, more preferably straight chain $C_9$-$C_{17}$ alkyl or alkenyl, most preferably straight chain $C_{11}$-$C_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, and alkoxylated derivatives thereof, where n is an integer from 3 to 5, inclusive, and R' is H or a cyclic or aliphatic monosaccharide. Most preferred are glycityls wherein n is 4, particularly —$CH_2$—$(CHOH)_4$—$CH_2OH$.

R' can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

Diamines—The preferred liquid detergent compositions, such as light duty liquid, LDL compositions, useful in the methods of the present invention may further comprise one or more diamines, preferably an amount of diamine such that the ratio of anionic surfactant present to the diamine is from about 40:1 to about 2:1. Said diamines provide for increased removal of grease and greasy food material while maintaining suitable levels of suds.

The diamines suitable for use in the compositions of the present invention have the formula:

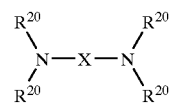

wherein each $R^{20}$ is independently selected from the group consisting of hydrogen, $C_1$-$C_4$ linear or branched alkyl, alkyleneoxy having the formula:

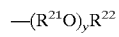

wherein $R^{21}$ is $C_2$-$C_4$ linear or branched alkylene, and mixtures thereof; $R^{22}$ is hydrogen, $C_1$-$C_4$ alkyl, and mixtures thereof; y is from 1 to about 10; X is a unit selected from:

i) $C_3$-$C_{10}$ linear alkylene, $C_3$-$C_{10}$ branched alkylene, $C_3$-$C_{10}$ cyclic alkylene, $C_3$-$C_{10}$ branched cyclic alkylene, an alkyleneoxyalkylene having the formula:

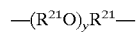

wherein $R^{21}$ and y are the same as defined herein above;

ii) $C_3$-$C_{10}$ linear, $C_3$-$C_{10}$ branched linear, $C_3$-$C_{10}$ cyclic, $C_3$-$C_{10}$ branched cyclic alkylene, $C_6$-$C_{10}$ arylene, wherein said unit comprises one or more electron donating or electron withdrawing moieties which provide said diamine with a $pK_a$ greater than about 8; and iii) mixtures of (i) and (ii)

provided said diamine has a $pK_a$ of at least about 8.

The preferred diamines of the present invention have a $pK_1$ and $pK_2$ which are each in the range of from about 8 to about 11.5, preferably in the range of from about 8.4 to about 11, more preferably from about 8.6 to about 10.75. For the purposes of the present invention the term "$pK_a$" stands equally well for the terms "$pK_1$" and "$pK_2$" either separately or collectively. The term $pK_a$ as used herein throughout the present specification in the same manner as used by those of ordinary skill in the art. $pK_a$ values are readily obtained from standard literature sources, for example, "Critical Stability Constants: Volume 2, Amines" by Smith and Martel, Plenum Press, N.Y. and London, (1975).

As an applied definition herein, the $pK_a$ values of the diamines are specified as being measured in an aqueous solution at 25° C. having an ionic strength of from about 0.1 to about 0.5 M. As used herein, the $pK_a$ is an equilibrium constant dependent upon temperature and ionic strength, therefore, value reported by literature references, not measured in the above described manner, may not be within full agreement with the values and ranges which comprise the present invention. To eliminate ambiguity, the relevant conditions and/or references used for $pK_a$'s of this invention are as defined herein or in "Critical Stability Constants: Volume 2, Amines". One typical method of measurement is the potentiometric titration of the acid with sodium hydroxide and determination of the $pK_a$ by suitable methods as described and referenced in "The Chemist's Ready Reference Handbook" by Shugar and Dean, McGraw Hill, N.Y., 1990.

Preferred diamines for performance and supply considerations are 1,3-bis(methylamino)cyclohexane, 1,3-diaminopropane (pK$_1$=10.5; pK$_2$=8.8), 1,6-diaminohexane (pK$_1$=11; pK$_2$=10), 1,3-diaminopentane (Dytek EP) (pK$_1$=10.5; pK$_2$=8.9), 2-methyl 1,5-diaminopentane (Dytek A) (pK$_1$=11.2; pK$_2$=10.0). Other preferred materials are the primary/primary diamines having alkylene spacers ranging from C$_4$–C$_8$ In general, primary diamines are preferred over secondary and tertiary diamines.

The following are non-limiting examples of diamines suitable for use in the present invention.

1-N,N-dimethylamino-3-aminopropane having the formula:

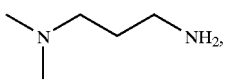

1,6-diaminohexane having the formula:

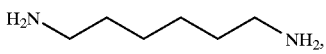

1,3-diaminopropane having the formula:

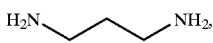

2-methyl-1,5-diaminopentane having the formula:

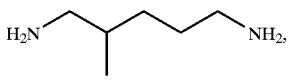

1,3-diaminopentane, available under the tradename Dytek EP, having the formula:

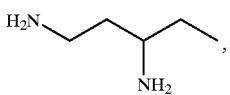

1,3-diaminobutane having the formula:

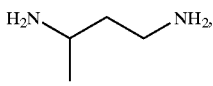

Jeffamine EDR 148, a diamine having an alkyleneoxy backbone, having the formula:

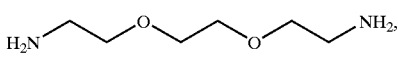

3-methyl-3-aminoethyl-5-dimethyl-1-aminocyclohexane (isophorone diamine) having the formula:

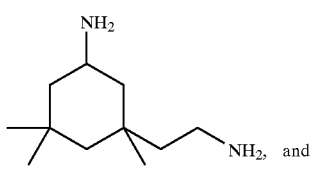

1,3-bis(methylamino)cyclohexane having the formula:

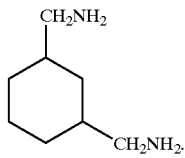

Additional Detergent Components

The following are non-limiting examples of additional detergent components (adjunct ingredients) useful in the bleaching compositions, especially laundry detergent compositions, of the present invention, said adjunct ingredients include builders, optical brighteners, soil release polymers, dye transfer agents, dispersants, enzymes, suds suppressers, dyes, perfumes, colorants, filler salts, hydrotropes, photoactivators, fluorescers, fabric conditioners, hydrolyzable surfactants, preservatives, antioxidants, chelants, stabilizers, anti-shrinkage agents, anti-wrinkle agents, germicides, fungicides, anti corrosion agents, and mixtures thereof.

Builders—The bleaching compositions of the present invention preferably comprise one or more detergent builders or builder systems. When present, the compositions will typically comprise at least about 1% builder, preferably from about 5%, more preferably from about 10% to about 80%, preferably to about 50%, more preferably to about 30% by weight, of detergent builder.

The level of builder can vary widely depending upon the end use of the composition and its desired physical form. When present, the compositions will typically comprise at least about 1% builder. Formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a SiO$_2$:Na$_2$O ratio in the range 1.6:1 to 3.2:1 and layered silicates, such as the layered sodium silicates described in U.S. Pat. No. 4,664,839 Rieck, issued May 12, 1987. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-Na$_2$SiO$_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula NaMSi$_x$O$_{2x+1}$.yH$_2$O wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-Na$_2$SiO$_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$[M_z(zAlO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "poly-carboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylate, including oxydisuccinate, as disclosed in U.S. Pat. No. 3,128,287 Berg, issued Apr. 7, 1964, U.S. Pat. No. 3,635,830 Lamberti et al., issued Jan. 18, 1972, and U.S. Pat. No. 3,936,448 Lamberti, issued Feb. 3, 1976. See also "TMS/TDS" builders of U.S. Pat. No. 4,663,071 Bush et al., issued May 5, 1987. Suitable ether polycarboxylates also include cyclic compounds, particularly alicyclic compounds, such as those described in U.S. Pat. No. 3,923,679 Rapko, issued Dec. 2, 1975; U.S. Pat. No. 4,158,635 Crutchfield et al., issued Jun. 19, 1979; U.S. Pat. No. 4,120,874 Crutchfield et al., issued Oct. 17, 1978; and U.S. Pat. No. 4,102,903 Crutchfield et al., issued Jul. 25, 1978.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the bleaching compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the C$_5$–C$_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al., issued Mar. 13, 1979 and in U.S. Pat. No. 3,308,067, Diehl, issued Mar. 7, 1967. See also Diehl U.S. Pat. No. 3,723,322.

Fatty acids, e.g., C$_{12}$–C$_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Chelating Agents—The bleaching compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Examples of suitable chelating agents and levels of use are described in U.S. Pat. Nos. 5,576,282 and 5,728,671.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder useful with, for example, insoluble builders such as zeolites, layered silicates and the like.

If utilized, these chelating agents will generally comprise from about 0.1% by weight of the bleaching compositions herein to about 15%, more preferably 3.0% by weight of the bleaching compositions herein.

Dye Transfer Inhibiting Agents—The bleaching compositions of the present invention may also include one or more compounds, dye transfer inhibiting agents, for inhibiting dye transfer from one fabric to another of solubilized and suspended dyes encountered during fabric laundering and conditioning operations involving colored fabrics.

Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Examples of such dye transfer inhibiting agents are disclosed in U.S. Pat. Nos. 5,707,950 and 5,707,951.

Additional suitable dye transfer inhibiting agents include, but are not limited to, cross-linked polymers. Cross-linked polymers are polymers whose backbone are interconnected to a certain degree; these links can be of chemical or physical nature, possibly with active groups on the backbone or on branches. Cross-linked polymers have been described in the Journal of Polymer Science, volume 22, pages 1035–1039.

In one embodiment, the cross-linked polymers are made in such a way that they form a three-dimensional rigid structure, which can entrap dyes in the pores formed by the three-dimensional structure.

In another embodiment, the cross-linked polymers entrap dyes by swelling.

Suitable cross-linked polymers are described in the co-pending European patent application 94870213.9.

Addition of such polymers also enhances the performance of the enzymes within the bleaching compositions herein.

The dye transfer inhibiting agents have the ability to complex or adsorb fugitive dyes wash out of dyed fabrics before the dyes have the opportunity to become attached to other articles in the wash.

When present in the bleaching compositions herein, the dye transfer inhibiting agents are present at levels from about 0.0001%, more preferably about 0.01%, most preferably about 0.05% by weight of the bleaching compositions to about 10%, more preferably about 2%, most preferably about 1% by weight of the bleaching compositions.

Dispersants—The bleaching compositions of the present invention can also contain dispersants. Suitable water-soluble organic salts are the homo- or co-polymeric acids or their salts, in which the polycarboxylic acid comprises at least two carboxyl radicals separated from each other by not more than two carbon atoms.

Polymers of this type are disclosed in GB-A-1,596,756. Examples of such salts are polyacrylates of MW 2000-5000 and their copolymers with maleic anhydride, such copolymers having a molecular weight of from 1,000 to 100,000.

Especially, copolymer of acrylate and methylacrylate such as the 480N having a molecular weight of 4000, at a level from 0.5–20% by weight of composition can be added in the detergent compositions of the present invention.

The compositions of the invention may contain a lime soap peptiser compound, which has a lime soap dispersing power (LSDP), as defined hereinafter of no more than 8, preferably no more than 7, most preferably no more than 6.

The lime soap peptiser compound is preferably present at a level from 0% to 20% by weight.

A numerical measure of the effectiveness of a lime soap peptiser is given by the lime soap dispersant power (LSDP) which is determined using the lime soap dispersant test as described in an article by H. C. Borghetty and C. A. Bergman, J. Am. Oil. Chem. Soc., volume 27, pages 88–90, (1950). This lime soap dispersion test method is widely used by practitioners in this art field being referred to, for example, in the following review articles; W. N. Linfield, Surfactant science Series, Volume 7, page 3; W. N. Linfield, Tenside surf. det., volume 27, pages 159–163, (1990); and M. K. Nagarajan, W. F. Masler, Cosmetics and Toiletries, volume 104, pages 71–73, (1989). The LSDP is the % weight ratio of dispersing agent to sodium oleate required to disperse the lime soap deposits formed by 0.025 g of sodium oleate in 30 ml of water of 333 ppm $CaCO_3$ (Ca:Mg=3:2) equivalent hardness.

Surfactants having good lime soap peptiser capability will include certain amine oxides, betaines, sulfobetaines, alkyl ethoxysulfates and ethoxylated alcohols.

Exemplary surfactants having a LSDP of no more than 8 for use in accord with the present invention include $C_{16}$–$C_{18}$ dimethyl amine oxide, $C_{12}$–$C_{18}$ alkyl ethoxysulfates with an average degree of ethoxylation of from 1–5, particularly $C_{12}$–$C_{15}$ alkyl ethoxysulfate surfactant with a degree of ethoxylation of amount 3 (LSDP=4), and the $C_{14}$–$C_{15}$ ethoxylated alcohols with an average degree of ethoxylation of either 12 (LSDP=6) or 30, sold under the tradenames Lutensol A012 and Lutensol A030 respectively, by BASF GmbH.

Polymeric lime soap peptisers suitable for use herein are described in the article by M. K. Nagarajan, W. F. Masler, to be found in Cosmetics and Toiletries, volume 104, pages 71–73, (1989).

Hydrophobic bleaches such as 4-[N-octanoyl-6-aminohexanoyl]benzene sulfonate, 4-[N-nonanoyl-6-aminohexanoyl]benzene sulfonate, 4-[N-decanoyl-6-aminohexanoyl]benzene sulfonate and mixtures thereof, and nonanoyloxy benzene sulfonate together with hydrophilic/hydrophobic bleach formulations can also be used as lime soap peptisers compounds.

Enzymes—The bleaching compositions can comprise in addition to the amylase of the present invention one or more detergent enzymes which provide cleaning performance and/or fabric care benefits. Such enzymes can include proteases, amylases, cellulases and lipases. They may be incorporated into the non-aqueous liquid bleaching compositions herein in the form of suspensions, "marumes" or "prills". Another suitable type of enzyme comprises those in the form of slurries of enzymes in nonionic surfactants, e.g., the enzymes marketed by Novo Nordisk under the tradename "SL" or the microencapsulated enzymes marketed by Novo Nordisk under the tradename "LDP." Suitable enzymes and levels of use are described in U.S. Pat. No. 5,576,282.

Enzymes added to the compositions herein in the form of conventional enzyme prills are especially preferred for use herein. Such prills will generally range in size from about 100 to 1,000 microns, more preferably from about 200 to 800 microns and will be suspended throughout the non-aqueous liquid phase of the composition. Prills in the compositions of the present invention have been found, in comparison with other enzyme forms, to exhibit especially desirable enzyme stability in terms of retention of enzymatic activity over time. Thus, compositions which utilize enzyme prills need not contain conventional enzyme stabilizing such as must frequently be used when enzymes are incorporated into aqueous liquid detergents.

Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, known amylases, mannanases, xyloglucanases and mixtures thereof. A preferred combination is a bleaching composition having a cocktail of conventional applicable enzymes like protease, lipase, cutinase and/or cellulase in conjunction with the amylase of the present invention.

Examples of such suitable enzymes are disclosed in U.S. Pat. Nos. 5,576,282, 5,728,671 and 5,707,950

Suitable proteases are the subtilisins which are obtained from particular strains of B. subtilis and B. licheniformis (subtilisin BPN and BPN'). One suitable protease is obtained from a strain of Bacillus, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE®, DURAZYM® and SAVINASE® from Novo and MAXATASE®, MAXACAL®, PROPERASE® and MAXAPEM® (protein engineered Maxacal) from Gist-Brocades. Proteolytic enzymes also encompass modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine protealytic enzyme which is called "Protease A" herein. More preferred is what is called herein "Protease C", which is a variant of an alkaline serine protease from Bacillus in which lysine replaced arginine at position 27, tyrosine replaced valine at position 104, serine replaced asparagine at position 123, and alanine replaced threonine at position 274. Protease C is described in EP 90915958:4, corresponding to WO 91/06637, Published May 16, 1991. Genetically modified variants, particularly of Protease C, are also included herein. See also a high pH protease from Bacillus sp. NCIMB 40338 described in WO 93/18140 A to Novo. Enzymatic detergents comprising protease, one or more other enzymes, and a reversible protease inhibitor are described in WO 92/03529 A to Novo. When desired, a protease having decreased adsorption and increased hydrolysis is available as described in WO 95/07791 to Procter & Gamble. A recombinant trypsin-like protease for detergents suitable herein is described in WO 94/25583 to Novo.

In more detail, the protease referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of Bacillus amyloliquefaciens subtilisin, as described in WO 95/10615 published Apr. 20, 1995 by Genencor International. Also suitable for the present invention are proteases described in patent applications EP 251 446 and WO91/06637 and protease BLAP® described in WO91/02792. The proteolytic enzymes are incorporated in the bleaching compositions of the present invention a level of from 0.0001% to 2%, preferably from 0.001% to 0.2%, more preferably from 0.005% to 0.1% pure enzyme by weight of the composition.

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Other particularly useful proteases are multiply-substituted protease variants comprising a substitution of an amino acid residue with another naturally occurring amino acid residue at an amino acid residue position corresponding to position 103 of Bacillus amyloliquefaciens subtilisin in combination with a substitution of an amino acid residue with another naturally occurring amino acid residue at one or more amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of Bacillus amyloliquefaciens subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 of Bacillus amyloliquefaciens subtilisin and/or multiply-substituted protease variants comprising a substitution of an amino acid residue with another naturally occurring amino acid residue at one or more amino acid residue positions corresponding to positions 62, 212, 230, 232, 252 and 257 of Bacillus amyloliquefaciens subtilisin as described in PCT Published Application Nos. WO 99/20727, WO 99/20726, and WO 99/20723 all owned by The Procter & Gamble Company.

More preferably the protease variant includes a substitution set selected from the group consisting of:

12/76/103/104/130/222/245/261;
62/103/104/159/232/236/245/248/252;
62/103/104/159/213/232/236/245/248/252;
62/101/103/104/159/212/213/232/236/245/248/252;
68/103/104/159/232/236/245;
68/103/104/159/230/232/236/245;
68/103/104/159/209/232/236/245;
68/103/104/159/232/236/245/257;
68/76/103/104/159/213/232/236/245/260;
68/103/104/159/213/232/236/245/248/252;
68/103/104/159/183/232/236/245/248/252;
68/103/104/159/185/232/236/245/248/252;
68/103/104/159/185/210/232/236/245/248/252;
68/103/104/159/210/232/236/245/248/252;
68/103/104/159/213/232/236/245;
98/103/104/159/232/236/245/248/252;
98/102/103/104/159/212/232/236/245/248/252;
101/103/104/159/232/236/245/248/252;
102/103/104/159/232/236/245/248/252;

-continued

103/104/159/230/236/245;
103/104/159/232/236/245/248/252;
103/104/159/217/232/236/245/248/252;
103/104/130/159/232/236/245/248/252;
103/104/131/159/232/236/245/248/252;
103/104/159/213/232/236/245/248/252; and
103/104/159/232/236/245.

Still even more preferably the protease variant includes a substitution set selected from the group consisting of:

12R/76D/103A/104T/130T/222S/245R/261D;
62D/103A/104I/159D/232V/236H/245R/248D/252K;
62D/103A/104I/159D/213R/232V/236H/245R/248D/252K;
68A/103A/104I/159D/209W/232V/236H/245R;
68A/76D/103A/104I/159D/213R/232V/236H/245R/260A;
68A/103A/104I/159D/213E/232V/236H/245R/248D/252K;
68A/103A/104I/159D/183D/232V/236H/245R/248D/252K;
68A/103A/104I/159D/232V/236H/245R;
68A/103A/104I/159D/230V/232V/236H/245R;
68A/103A/104I/159D/232V/236H/245R/257V;
68A/103A/104I/159D/213G/232V/236H/245R/248D/252K;
68A/103A/104I/159D/185D/232V/236H/245R/248D/252K;
68A/103A/104I/159D/185D/210L/232V/236H/245R/248D/252K;
68A/103A/104I/159D/210L/232V/236H/245R/248D/252K;
68A/103A/104I/159D/213G/232V/236H/245R;
98L/103A/104I/159D/232V/236H/245R/248D/252K;
98L/102A/103A/104I/159D/212G/232V/236H/245R/248D/252K;
101G/103A/104I/159D/232V/236H/245R/248D/252K;
102A/103A/104I/159D/232V/236H/245R/248D/252K;
103A/104I/159D/230V/236H/245R;
103A/104I/159D/232V/236H/245R/248D/252K;
103A/104I/159D/217E/232V/236H/245R/248D/252K;
103A/104I/130G/159D/232V/236H/245R/248D/252K;
103A/104I/131V/159D/232V/236H/245R/248D/252K;
103A/104I/159D/213R/232V/236H/245R/248D/252K; and
103A/104I/159D/232V/236H/245R.

Most preferably the protease variant includes the substitution set 101/103/104/159/232/236/245/248/252, preferably 101 G/103A/104I/159D/232V/236H/245R/248D/252K.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from *Humicola insolens*. Suitable cellulases are also disclosed in GB-A-2.075.028; GB-A-2.095.275 and DE-OS-2.247.832.

Examples of such cellulases are cellulases produced by a strain of *Humicola insolens* (*Humicola grisea* var. *thermoidea*), particularly the *Humicola* strain DSM 1800.

Other suitable cellulases are cellulases originated from *Humicola insolens* having a molecular weight of about 50 KDa, an isoelectric point of 5.5 and containing 415 amino acids; and a ~43 kD endoglucanase derived from *Humicola insolens*, DSM 1800, exhibiting cellulase activity; a preferred endoglucanase component has the amino acid sequence disclosed in PCT Patent Application No. WO 91/17243. Also suitable cellulases are the EGIII cellulases from *Trichoderma longibrachiatum* described in WO94/21801, Genencor, published Sep. 29, 1994. Especially suitable cellulases are the cellulases having color care benefits. Examples of such cellulases are cellulases described in European patent application No. 91202879.2, filed Nov. 6, 1991 (Novo). Carezyme and Celluzyme (Novo Nordisk A/S) are especially useful. See also WO91/17243.

Peroxidase enzymes are known in the art, and include, for example, horseradish peroxidase, ligninase and haloperoxidase such as chloro- and bromo-peroxidase. Peroxidase-containing bleaching compositions are disclosed, for example, in U.S. Pat. Nos. 5,576,282, 5,728,671 and 5,707,950, PCT International Applications WO 89/099813, WO89/09813 and in European Patent application EP No. 91202882.6, filed on Nov. 6, 1991 and EP No. 96870013.8, filed Feb. 20, 1996. Also suitable is the laccase enzyme.

Preferred enhancers are substituted phenthiazine and phenoxasine 10-Phenothiazinepropionicacid (PPT), 10-ethylphenothiazine-4-carboxylic acid (EPC), 10-phenoxazinepropionic acid (POP) and 10-methylphenoxazine (described in WO 94/12621) and substituted syringates ($C_3$–$C_5$ substituted alkyl syringates) and phenols. Sodium percarbonate or perborate are preferred sources of hydrogen peroxide.

Said peroxidases are normally incorporated in the bleaching composition at levels from 0.0001% to 2% of active enzyme by weight of the bleaching composition.

Other preferred enzymes that can be included in the bleaching compositions of the present invention include lipases. Suitable lipase enzymes for detergent usage include those produced by microorganisms of the *Pseudomonas* group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. Especially suitable lipases are lipases such as M1 LIPASE® and LIPOMAX® (Gist-Brocades) and LIPOLASE® and LIPOLASE ULTRA® (Novo) which have found to be very effective when used in combination with the compositions of the present invention.

Also suitable are cutinases [EC 3.1.1.50] which can be considered as a special kind of lipase, namely lipases which do not require interfacial activation. Addition of cutinases to bleaching compositions have been described in e.g. WO 88/09367 (Genencor).

The lipases and/or cutinases are normally incorporated in the bleaching composition at levels from 0.0001% to 2% of active enzyme by weight of the bleaching composition.

Known amylases ($\alpha$ and/or $\beta$) can be included for removal of carbohydrate-based stains. WO 94/02597, Novo Nordisk A/S published Feb. 3, 1994, describes cleaning compositions which incorporate mutant amylases. See also WO94/18314, Genencor, published Aug. 18, 1994 and WO95/10603, Novo Nordisk A/S, published Apr. 20, 1995. Other amylases known for use in bleaching compositions include both $\alpha$- and $\beta$-amylases. $\alpha$-Amylases are known in the art and include those disclosed in U.S. Pat. No. 5,003,257; EP 252,666; WO 91/00353; FR 2,676,456; EP 285,123; EP 525,610; EP 368,341; and British Patent Specification No. 1,296,839 (Novo). Other suitable amylase are stability-enhanced amylases including PURAFACT OX AM® described in WO 94/18314, published Aug. 18, 1994 and WO96/05295, Genencor, published Feb. 22, 1996 and amylase variants from Novo Nordisk A/S, disclosed in WO 95/10603, published April 95.

Examples of commercial $\alpha$-amylases products are TERMAMYL®, BAN®, FUNGAMYL® and DURAMYL®, all available from Novo Nordisk A/S Denmark. WO95/26397 describes other suitable amylases: α-amylases characterized by having a specific activity at least 25% higher than the specific activity of TERMAMYL® at a temperature range of 25° C. to 55° C. and at a pH value in the range of 8 to 10, measured by the Phadebas® α-amylase activity assay. Other amylolytic enzymes with improved properties with respect to the activity level and the combination of thermostability and a higher activity level are described in WO95/35382.

The compositions of the present invention may also comprise a mannanase enzyme. Preferably, the mannanase is selected from the group consisting of: three mannans-degrading enzymes: EC 3.2.1.25: β-mannosidase, EC 3.2.1.78: Endo-1,4-β-mannosidase, referred therein after as "mannanase" and EC 3.2.1.100: 1,4-β-mannobiosidase and mixtures thereof. (IUPAC Classification-Enzyme nomenclature, 1992 ISBN 0-12-227165-3 Academic Press).

More preferably, the treating compositions of the present invention, when a mannanase is present, comprise a α-1,4-Mannosidase (E.C. 3.2.1.78) referred to as Mannanase. The term "mannanase" or "galactomannanase" denotes a mannanase enzyme defined according to the art as officially being named mannan endo-1,4-beta-mannosidase and having the alternative names beta-mannanase and endo-1,4-mannanase and catalysing the reaction: random hydrolysis of 1,4-beta-D-mannosidic linkages in mannans, galactomannans, glucomannans, and galactoglucomannans.

In particular, Mannanases (EC 3.2.1.78) constitute a group of polysaccharases which degrade mannans and denote enzymes which are capable of cleaving polyose chains containing mannose units, i.e. are capable of cleaving glycosidic bonds in mannans, glucomannans, galactomannans and galactogluco-mannans. Mannans are polysaccharides having a backbone composed of β-1,4-linked mannose; glucomannans are polysaccharides having a backbone or more or less regularly alternating β-1,4 linked mannose and glucose; galactomannans and galactoglucomannans are mannans and glucomannans with α-1,6 linked galactose sidebranches. These compounds may be acetylated.

The degradation of galactomannans and galactoglucomannans is facilitated by full or partial removal of the galactose sidebranches. Further the degradation of the acetylated mannans, glucomannans, galactomannans and galactogluco-mannans is facilitated by full or partial deacetylation. Acetyl groups can be removed by alkali or by mannan acetylesterases. The oligomers which are released from the mannanases or by a combination of mannanases and α-galactosidase and/or mannan acetyl esterases can be further degraded to Telease free maltose by β-mannosidase and/or β-glucosidase.

Mannanases have been identified in several Bacillus organisms. For example, Talbot et al., Appl. Environ. Microbiol., Vol. 56, No. 11, pp. 3505–3510 (1990) describes a beta-mannanase derived from Bacillus stearothermophilus in dimer form having molecular weight of 162 kDa and an optimum pH of 5.5–7.5. Mendoza et al., World J. Microbiol. Biotech., Vol. 10, No. 5, pp. 551–555 (1994) describes a beta-mannanase derived from Bacillus subtilis having a molecular weight of 38 kDa, an optimum activity at pH 5.0 and 55C and a pI of 4.8. JP-03047076 discloses a beta-mannanase derived from Bacillus sp., having a molecular weight of 373 kDa measured by gel filtration, an optimum pH of 8–10 and a pI of 5.3–5.4. JP-63056289 describes the production of an alkaline, thermostable beta-mannanase which hydrolyses beta-1,4-D-mannopyranoside bonds of e.g. mannans and produces manno-oligosaccharides. JP-63036774 relates to the Bacillus microorganism FERM P-8856 which produces beta-mannanase and beta-mannosidase at an alkaline pH. JP-08051975 discloses alkaline beta-mannanases from alkalophilic Bacillus sp. AM-001. A purified mannanase from Bacillus amyloliquefaciens useful in the bleaching of pulp and paper and a method of preparation thereof is disclosed in WO 97/11164. WO 91/18974 describes a hemicellulase such as a glucanase, xylanase or mannanase active at an extreme pH and temperature. WO 94/25576 discloses an enzyme from Aspergillus aculeatus, CBS 101.43, exhibiting mannanase activity which may be useful for degradation or modification of plant or algae cell wall material. WO 93/24622 discloses a mannanase isolated from Trichoderma reseei useful for bleaching lignocellulosic pulps. An hemicellulase capable of degrading mannan-containing hemicellulose is described in WO91/18974 and a purified mannanase from Bacillus amyloliquefaciens is described in WO97/11164.

Preferably, the mannanase enzyme will be an alkaline mannanase as defined below, more preferably, a mannanase originating from a bacterial source. Especially, the laundry detergent composition of the present invention will comprise an alkaline mannanase selected from the mannanase from the strain Bacillus agaradhaerens NICMB 40482; the mannanase from Bacillus subtilis strain 168, gene yght; the mannanase from Bacillus sp. 1633 and/or the mannanase from Bacillus sp. AAI12. Most preferred mannanase for the inclusion in the detergent compositions of the present invention is the mannanase enzyme originating from Bacillus sp. 1633 as described in the co-pending Danish patent application No. PA 1998 01340.

The terms "alkaline mannanase enzyme" is meant to encompass an enzyme having an enzymatic activity of at least 10%, preferably at least 25%, more preferably at least 40% of its maximum activity at a given pH ranging from 7 to 12, preferably 7.5 to 10.5.

The alkaline mannanase from Bacillus agaradhaerens NICMB 40482 is described in the co-pending U.S. patent application Ser. No. 09/111,256. More specifically, this mannanase is:

i) a polypeptide produced by Bacillus agaradhaerens, NCIMB 40482; or ii) a polypeptide comprising an amino acid sequence as shown in positions 32–343 of SEQ ID NO:2 as shown in U.S. patent application Ser. No. 09/111,256; or iii) an analogue of the polypeptide defined in i) or ii) which is at least 70% homologous with said polypeptide, or is derived from said polypeptide by substitution, deletion or addition of one or several amino acids, or is immunologically reactive with a polyclonal antibody raised against said polypeptide in purified form.

Also encompassed is the corresponding isolated polypeptide having mannanase activity selected from the group consisting of:

(a) polynucleotide molecules encoding a polypeptide having mannanase activity and comprising a sequence of nucleotides as shown in SEQ ID NO: 1 from nucleotide 97 to nucleotide 1029 as shown in U.S. patent application Ser. No. 09/111,256;

(b) species homologs of (a);

(c) polynucleotide molecules that encode a polypeptide having mannanase activity that is at least 70% identical to the amino acid sequence of SEQ ID NO: 2 from amino acid residue 32 to amino acid residue 343 as shown in U.S. patent application Ser. No. 09/111,256;

(d) molecules complementary to (a), (b) or (c); and (e) degenerate nucleotide sequences of (a), (b), (c) or (d).

The plasmid pSJ1678 comprising the polynucleotide molecule (the DNA sequence) encoding said mannanase has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on 18 May 1998 under the deposition number DSM 12180.

A second more preferred enzyme is the mannanase from the *Bacillus subtilis* strain 168, which is described in the co-pending U.S. patent application Ser. No. 09/095,163. More specifically, this mannanase is:

i) is encoded by the coding part of the DNA sequence shown in SEQ ID No. 5 shown in the U.S. patent application Ser. No. 09/095,163 or an analogue of said sequence; and/or ii) a polypeptide comprising an amino acid sequence as shown SEQ ID NO:6 shown in the U.S. patent application Ser. No. 09/095,163; or iii) an analogue of the polypeptide defined in ii) which is at least 70% homologous with said polypeptide, or is derived from said polypeptide by substitution, deletion or addition of one or several amino acids, or is immunologically reactive with a polyclonal antibody raised against said polypeptide in purified form.

Also encompassed in the corresponding isolated polypeptide having mannanase activity selected from the group consisting of:

(a) polynucleotide molecules encoding a polypeptide having mannanase activity and comprising a sequence of nucleotides as shown in SEQ ID NO:5 as shown in the U.S. patent application Ser. No. 09/095,163

(b) species homologs of (a);

(c) polynucleotide molecules that encode a polypeptide having mannanase activity that is at least 70% identical to the amino acid sequence of SEQ ID NO: 6 as shown in the U.S. patent application Ser. No. 09/095,163;

(d) molecules complementary to (a), (b) or (c); and (e) degenerate nucleotide sequences of (a), (b), (c) or (d).

A third more preferred mannanase is described in the co-pending Danish patent application No. PA 1998 01340. More specifically, this mannanase is:

i) a polypeptide produced by *Bacillus* sp. 1633;

ii) a polypeptide comprising an amino acid sequence as shown in positions 33–340 of SEQ ID NO:2 as shown in the Danish application No. PA 1998 01340; or iii) an analogue of the polypeptide defined in i) or ii) which is at least 65% homologous with said polypeptide, is derived from said polypeptide by substitution, deletion or addition of one or several amino acids, or is immunologically reactive with a polyclonal antibody raised against said polypeptide in purified form.

Also encompassed is the corresponding isolated polynucleotide molecule selected from the group consisting of:

(a) polynucleotide molecules encoding a polypeptide having mannanase activity and comprising a sequence of nucleotides as shown in SEQ ID NO: 1 from nucleotide 317 to nucleotide 1243 the Danish application No. PA 1998 01340;

(b) species homologs of (a);

(c) polynucleotide molecules that encode a polypeptide having mannanase activity that is at least 65% identical to the amino acid sequence of SEQ ID NO: 2 from amino acid residue 33 to amino acid residue 340 the Danish application No. PA 1998 01340;

(d) molecules complementary to (a), (b) or (c); and (e) degenerate nucleotide sequences of (a), (b), (c) or (d).

The plasmid pBXM3 comprising the polynucleotide molecule (the DNA sequence) encoding a mannanase of the present invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on 29 May 1998 under the deposition number DSM 12197.

A fourth more preferred mannanase is described in the Danish co-pending patent application No. PA 1998 01341. More specifically, this mannanase is:

i) a polypeptide produced by *Bacillus* sp. AAI 12;

ii) a polypeptide comprising an amino acid sequence as shown in positions 25–362 of SEQ ID NO:2 as shown in the Danish application No. PA 1998 01341; or iii) an analogue of the polypeptide defined in i) or ii) which is at least 65% homologous with said polypeptide, is derived from said polypeptide by substitution, deletion or addition of one or several amino acids, or is immunologically reactive with a polyclonal antibody raised against said polypeptide in purified form.

Also encompassed is the corresponding isolated polynucleotide molecule selected from the group consisting of (a) polynucleotide molecules encoding a polypeptide having mannanase activity and comprising a sequence of nucleotides as shown in SEQ ID NO: 1 from nucleotide 225 to nucleotide 1236 as shown in the Danish application No. PA 1998 01341;

(b) species homologs of (a);

(c) polynucleotide molecules that encode a polypeptide having mannanase activity that is at least 65% identical to the amino acid sequence of SEQ ID NO: 2 from amino acid residue 25 to amino acid residue 362 as shown in the Danish application No. PA 1998 01341;

(d) molecules complementary to (a), (b) or (c); and (e) degenerate nucleotide sequences of (a), (b), (c) or (d).

The plasmid pBXM1 comprising the polynucleotide molecule (the DNA sequence) encoding a mannanase of the present invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on 7 Oct. 1998 under the deposition number DSM 12433.

The mannanase, when present, is incorporated into the treating compositions of the present invention preferably at a level of from 0.0001% to 2%, more preferably from 0.0005% to 0.1%, most preferred from 0.001% to 0.02% pure enzyme by weight of the composition.

The compositions of the present invention may also comprise a xyloglucanase enzyme. Suitable xyloglucanases for the purpose of the present invention are enzymes exhibiting endoglucanase activity specific for xyloglucan, preferably at a level of from about 0.001% to about 1%, more preferably from about 0.01% to about 0.5%, by weight of the composition. As used herein, the term "endoglucanase activity" means the capability of the enzyme to hydrolyze 1,4-

β-D-glycosidic linkages present in any cellulosic material, such as cellulose, cellulose derivatives, lichenin, β-D-glucan, or xyloglucan. The endoglucanase activity may be determined in accordance with methods known in the art, examples of which are described in WO 94/14953 and hereinafter. One unit of endoglucanase activity (e.g. CMCU, AVIU, XGU or BGU) is defined as the production of 1 μmol reducing sugar/min from a glucan substrate, the glucan substrate being, e.g., CMC (CMCU), acid swollen Avicell (AVIU), xyloglucan (XGU) or cereal β-glucan (BGU). The reducing sugars are determined as described in WO 94/14953 and hereinafter. The specific activity of an endoglucanase towards a substrate is defined as units/mg of protein.

Suitable are enzymes exhibiting as its highest activity XGU endoglucanase activity (hereinafter "specific for xyloglucan"), which enzyme:

i) is encoded by a DNA sequence comprising or included in at least one of the following partial sequences

```
(a) ATTCATTTGT GGACAGTGGA C                                    (SEQ ID No: 1)

(b) GTTGATCGCA CATTGAACCA                                      (SEQ ID NO: 2)

(c) ACCCCAGCCG ACCGATTGTC                                      (SEQ ID NO: 3)

(d) CTTCCTTACC TCACCATCAT                                      (SEQ ID NO: 4)

(e) TTAACATCTT TTCACCATGA                                      (SEQ ID NO: 5)

(f) AGCTTTCCCT TCTCTCCCTT                                      (SEQ ID NO: 6)

(g) GCCACCCTGG CTTCCGCTGC CAGCCTCC                             (SEQ ID NO: 7)

(h) GACAGTAGCA ATCCAGCATT                                      (SEQ ID NO: 8)

(i) AGCATCAGCC GCTTTGTACA                                      (SEQ ID NO: 9)

(j) CCATGAAGTT CACCGTATTG                                      (SEQ ID NO: 10)

(k) GCACTGCTTC TCTCCCAGGT                                      (SEQ ID NO: 11)

(l) GTGGGCGGCC CCTCAGGCAA                                      (SEQ ID NO: 12)

(m) ACGCTCCTCC AATTTTCTCT                                      (SEQ ID NO: 13)

(n) GGCTGGTAG TAATGAGTCT                                       (SEQ ID NO: 14)

(o) GGCGCAGAGT TTGGCCAGGC                                      (SEQ ID NO: 15)

(p) CAACATCCCC GGTGTTCTGG G                                    (SEQ ID NO: 16)

(q) AAAGATTCAT TTGTGGACAG TGGACGTTGA TCGCACATTG AACCAACCCC(SEQ ID NO:17)
    AGCCGACCGA

TTGTCCTTCC TTACCTCACC ATCATTTAAC ATCTTTTCAC CATGAAGCTT
    TCCCTTCTCT

CCCTTGCCAC CCTGGCTTCC GCTGCCAGCC TCCAGCGCCG CACACTTCTG
    CGGTCAGTGG

GATACCGCCA CCGCCGGTGA CTTCACCCTG TACAACGACC TTTGGGGCGA
    GACGGCCGGC

ACCGGCTCCC AGTGCACTGG AGTCGACTCC TACAGCGGCG ACACCATCGC
    TTGTCACACC

AGCAGGTCCT GGTCGGAGTA GCAGCAGCGT CAAGAGCTAT GCCAACG or (r) CAGCATCTCC ATTGAGTAAT CACGTTGGTG TTCGGTGGCC CGCCGTGTTG
    CGTGGCGGAG

GCTGCCGGGA GACGGGTGGG GATGGTGGTG GGAGAGAATG TAGGGCGCCG
    TGTTTCAGTC

CCTAGGCAGG ATACCGGAAA ACCGTGTGGT AGGAGGTTTA TAGGTTTCCA
    GGAGACGCTG

TATAGGGGAT AAATGAGATT GAATGGTGGC CACACTCAAA CCAACCAGGT
    CCTGTACATA

CAATGCATAT ACCAATTATA CCTACCAAAA AAAAAAAAA AAAAAAAAAA(SEQ ID NO:18)
    AAAA
``` or a sequence homologous thereto encoding a polypeptide specific for xyloglucan with endoglucanase activity, ii) is immunologically reactive with an antibody raised against a highly purified endoglucanase encoded by the DNA sequence defined in i) and derived from *Aspergillus aculeatus*, CBS 101.43, and is specific for xyloglucan.

More specifically, as used herein the term "specific for xyloglucan" means that the endoglucanse enzyme exhibits its highest endoglucanase activity on a xyloglucan substrate, and preferably less than 75% activity, more preferably less than 50% activity, most preferably less than about 25% activity, on other cellulose-containing substrates such as carboxymethyl cellulose, cellulose, or other glucans.

Preferably, the specificity of an endoglucanase towards xyloglucan is further defined as a relative activity determined as the release of reducing sugars at optimal conditions obtained by incubation of the enzyme with xyloglucan and the other substrate to be tested, respectively. For instance, the specificity may be defined as the xyloglucan to β-glucan activity (XGU/BGU), xyloglucan to carboxy methyl cellulose activity (XGU/CMCU), or xyloglucan to acid swollen Avicell activity (XGU/AVIU), which is preferably greater than about 50, such as 75, 90 or 100.

The term "derived from" as used herein refers not only to an endoglucanase produced by strain CBS 101.43, but also an endoglucanase encoded by a DNA sequence isolated from strain CBS 101.43 and produced in a host organism transformed with said DNA sequence. The term "homologue" as used herein indicates a polypeptide encoded by DNA which hybridizes to the same probe as the DNA coding for an endoglucanase enzyme specific for xyloglucan under certain specified conditions (such as presoaking in 5×SSC and prehybridizing for 1 h at −40° C. in a solution of 5×SSC, 5× Denhardt's solution, and 50 $\mu$g of denatured sonicated calf thymus DNA, followed by hybridization in the same solution supplemented with 50 $\mu$Ci 32-P-dCTP labeled probe for 18 h at −40° C. and washing three times in 2×SSC, 0.2% SDS at 40° C. for 30 minutes). More specifically, the term is intended to refer to a DNA sequence which is at least 70% homologous to any of the sequences shown above encoding an endoglucanase specific for xyloglucan, including at least 75%, at least 80%, at least 85%, at least 90% or even at least 95% with any of the sequences shown above. The term is intended to include modifications of any of the DNA sequences shown above, such as nucleotide substitutions which do not give rise to another amino acid sequence of the polypeptide encoded by the sequence, but which correspond to the codon usage of the host organism into which a DNA construct comprising any of the DNA sequences is introduced or nucleotide substitutions which do give rise to a different amino acid sequence and therefore, possibly, a different amino acid sequence and therefore, possibly, a different protein structure which might give rise to an endoglucanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

Endoglucanase specific for xyloglucan useful in the present invention preferably is one which has a XGU/BGU, XGU/CMU and/or XGU/AVIU ratio (as defined above) of more than 50, such as 75, 90 or 100.

Furthermore, the endoglucanase specific for xyloglucan is preferably substantially devoid of activity towards β-glucan and/or exhibits at the most 25% such as at the most 10% or about 5%, activity towards carboxymethyl cellulose and/or Avicell when the activity towards xyloglucan is 100%. In addition, endoglucanase specific for xyloglucan of the invention is preferably substantially devoid of transferase activity, an activity which has been observed for most endoglucanases specific for xyloglucan of plant origin.

Endoglucanase specific for xyloglucan may be obtained from the fungal species *A. aculeatus*, as described in WO 94/14953. Microbial endoglucanases specific for xyloglucan has also been described in WO 94/14953. Endoglucanases specific for xyloglucan from plants have been described, but these enzymes have transferase activity and therefore must be considered inferior to microbial endoglucanses specific for xyloglucan whenever extensive degradation of xyloglucan is desirable. An additional advantage of a microbial enzyme is that it, in general, may be produced in higher amounts in a microbial host, than enzymes of other origins.

The xyloglucanase, when present, is incorporated into the treating compositions of the invention preferably at a level of from 0.0001% to 2%, more preferably from 0.0005% to 0.1%, most preferred from 0.001% to 0.02% pure enzyme by weight of the composition.

The above-mentioned enzymes may be of any suitable origin, such as vegetable, animal, bacterial, fungal and yeast origin. Purified or non-purified forms of these enzymes may be used. Also included by definition, are mutants of native enzymes. Mutants can be obtained e.g. by protein and/or genetic engineering, chemical and/or physical modifications of native enzymes. Common practice as well is the expression of the enzyme via host organisms in which the genetic material responsible for the production of the enzyme has been cloned.

Said enzymes are normally incorporated in the bleaching composition at levels from 0.0001% to 2% of active enzyme by weight of the bleaching composition. The enzymes can be added as separate single ingredients (prills, granulates, stabilized liquids, etc. containing one enzyme) or as mixtures of two or more enzymes (e.g. cogranulates).

Other suitable detergent ingredients that can be added are enzyme oxidation scavengers. Examples of such enzyme oxidation scavengers are ethoxylated tetraethylene polyamines.

A range of enzyme materials and means for their incorporation into synthetic bleaching compositions is also disclosed in WO 93/07263 and WO 93/07260 to Genencor International, WO 89/08694 to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981.

Enzyme Stabilizers—Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful *Bacillus*, sp. AC13 giving proteases, xylanases and cellulases, is described in WO 9401532 to Novo. The enzymes employed herein can be stabilized by the presence of water-soluble sources of calcium and/or magnesium ions in the finished compositions which provide such ions to the enzymes. Suitable enzyme stabilizers and levels of use are described in U.S. Pat. No. 5,576,282.

Other Detergent Ingredients—The bleaching compositions herein may also optionally contain one or more of the following: polymeric dispersing agents, clay soil removal/anti-redeposition agents, brighteners, suds suppressors, dyes, perfumes, structure elasticizing agents, fabric softeners, carriers, hydrotropes, processing aids and/or pigments. Suitable examples of such other detergent ingredients and levels of use are found in U.S. Pat. No. 5,576,282.

Methods of Cleaning—In addition to the methods for cleaning fabrics, dishes and other hard surfaces, and body parts by personal cleansing, described herein, the invention herein also encompasses a laundering pretreatment process for fabrics which have been soiled or stained comprising directly contacting said stains and/or soils with a highly concentrated form of the bleaching composition set forth above prior to washing such fabrics using conventional aqueous washing solutions. Preferably, the bleaching composition remains in contact with the soil/stain for a period of from about 30 seconds to 24 hours prior to washing the pretreated soiled/stained substrate in conventional manner. More preferably, pretreatment times will range from about 1 to 180 minutes.

The following examples are meant to exemplify compositions of the present invention, but are not necessarily meant to limit or otherwise define the scope of the invention.

In the following examples some abbreviations known to those of ordinary skill in the art are used, consistent with the disclosure set forth herein.

SYNTHESIS EXAMPLES

Example I

Preparation of 1-(4,5-dihydro-3H-2-benzazepinium)-propane-3-sulfate (4):

Step 1: Preparation of 4,5-dihydro-3H-2-benzazepine (2):

A 100 mL round-bottom flask equipped with magnetic stir bar and distillation apparatus is charged with 3-phenylpropylamine (1, 24.8 g, 0.18 mol) and 88% formic acid (41.4 g, 0.79 mol, 4.4 equiv.) and the reaction is distilled at 150° C. Beginning after one hour, additional 8 ml aliquots of 88% formic acid are added over a 2 h period until the 3-phenylpropylamine is consumed, as monitored by gas chromatography. The reaction mixture is distilled (using a Dean-Stark trap) at 200° C. for 3 hours after which it is allowed to cool to room temperature.

A 500 mL round-bottom flask equipped with overhead mechanical stirrer, reflux condenser, and addition funnel is charged with phosphorus pentoxide (38.6 g) and polyphosphoric acid (168 g). The mixture is stirred and heated at 180° C. for about 8 h, then cooled to 150° C. The cooled, crude 3-phenylpropylformamide prepared as described above is added dropwise to this mixture. On complete addition the reaction is heated and stirred at 170° C. overnight. The mixture is cooled to room temperature and diluted with ice water (1.0 L), washed with diethyl ether (500 mL) and cooled in a brine/ice bath while the pH is adjusted to 9 with saturated potassium hydroxide. The aqueous solution is extracted with ether (2×250 mL) and the pooled organics are dried over magnesium sulfate, filtered, and concentrated under reduced pressure to yield an oil which solidifies upon addition of ether/hexane, and filtered to give 2. The preparation is represented by the following reaction:

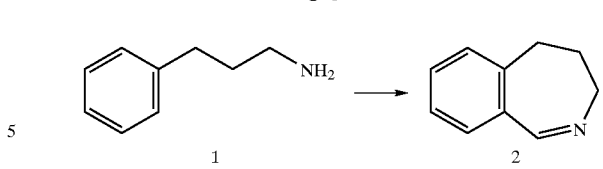

Step 2: 1-(4,5-dihydro-3H-2-benzazepinium)-propane-3-sulfate (4)

A 250 mL round-bottomed flask equipped with magnetic stir bar, argon inlet, addition funnel, and reflux condenser is charged with 4,5-dihydro-3H-2-benzazepine L2, 1.45 g, 10.0 mmol) and acetonitrile (10 mL). This mixture is cooled in an ice bath and charged dropwise with a solution of 1,3-propane sultone (2, 1.34 g, 11.0 mmol) in acetonitrile (5 mL). On complete addition the ice bath is removed and the reaction is heated to reflux overnight. The mixture is allowed to cool to room temperature and volatiles are removed under reduced pressure. The solid product is slurried and rinsed with acetone and allowed to air dry. The preparation is represented by the following reaction:

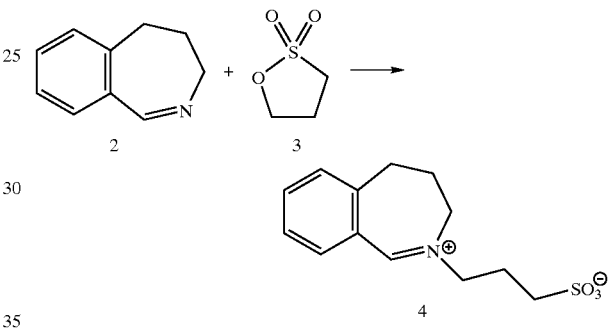

Example II

Preparation of N-Methyl-4,5-dihydro-3H-2-benzazepinium borontetrafluoride (4):

A 250 mL round-bottomed flask equipped with magnetic stir bar and argon inlet is charged with 4,5-dihydro-3H-2-benzazepine (2, 1.45 g, 10.0 mmol) and acetonitrile (10 mL). This mixture is cooled in an ice bath and charged dropwise with a solution of trimethyloxonium tetrafluoroborate (1.62 g, 11.0 mmol) in acetonitrile (5 mL). On complete addition the ice bath is removed and the reaction is stirred at room temperature overnight. The volatiles are removed under reduced pressure, and the solid product is slurried and rinsed with acetone and allowed to air dry. The preparation is represented by the following reaction:

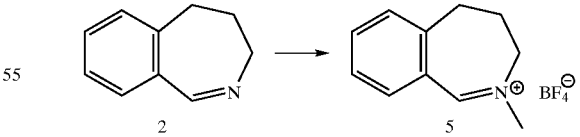

Example III

Preparation of 1-(8-chloro-3,4-dihydro-1-methyl-6-phenyl-1H-1,5-benzodiazocin-2-one)hexane-2-sulfate (9):

Step 1: Preparation of 1,2-hexanediol cyclic sulfate (7):

A 500 mL three-necked round-bottom flask equipped with mechanical stirrer, pressure equalizing addition funnel, and reflux condenser is charged with 1,2-hexanediol (6, 5.91 g, 50.0 mmol) and 50 mL of carbon tetrachloride. Upon dissolving of the 1,2-hexanediol, thionyl chloride (5.5 mL, 75 mmol) is added dropwise at room temperature, and the reaction is heated to 60° C. After 2 h, the reaction is cooled via ice bath. Water (50 mL) and acetonitrile (75 mL) are added. Ruthenium chloride hydrate (0.131 g, 0.50 mmol) and sodium periodate (21.4 g, 100 mmol) are added and the reaction mixture is stirred at room temperature for 1 h. The mixture is extracted with diethyl ether (4×175 mL), the organic layers are washed with water (5×100 mL), saturated sodium bicarbonate (3×100 mL), brine (2×100 mL), filtered through celite/silica gel, and dried over magnesium sulfate. The clear liquid is concentrated to give 7, a clear oil. The preparation is represented by the following reaction:

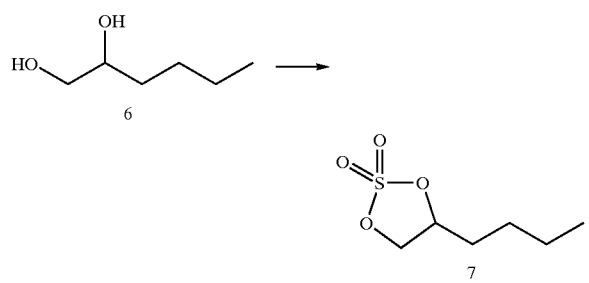

Step 2: Preparation of 8-chloro-3,4-dihydro-1-methyl-6-phenyl-1H-1,5-benzodiazocin-2-one (8) is as described in the art, as in Derieg, M. E. et al. *J. Org. Chem.* 1969, 34, 179.

Step 3: Preparation of 1-(8-chloro-3,4-dihydro-1-methyl-6-phenyl-1H-1,5-benzodiazocin-2-one)hexane-2-sulfate (9):

A 100 mL round-bottom flask equipped with magnetic stir bar is charged 8-chloro-3,4-dihydro-1-methyl-6-phenyl-1H-1,5-benzodiazocin-2-one (8, 1.98 g, 10.0 mmol) and acetonitrile (15 mL). To this solution is added in one portion 1,2-hexanediol cyclic sulfate (7, 1.30 g, 11.0 mmol). The reaction mixture becomes thick within 5 min, and additional acetonitrile (40 mL) is added. The reaction is stirred overnight. The precipitate is collected, washed with acetone, and allowed to air dry to give 9. The preparation is represented by the following reaction:

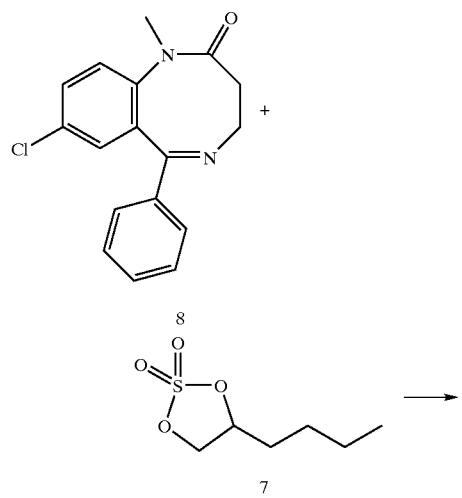

Example IV

Preparation of N-Methyl-1,2-oxydo-1,2,4,5-tetrahydro-3H-2-benzazepinium borontetrafluoride (11):

Step 1: Preparation of 1,2-oxydo-1,2,4,5-tetrahydro-3H-2-benzazepine (10):

A 500 mL round-bottomed flask equipped with magnetic stir bar and argon inlet is charged with 4,5-dihydro-3H-2-benzazepine (2, 14.5 g, 0.10 mol) and methanol (200 mL). The solution is cooled in an ice bath and m-chloroperoxybenzoic acid (1.0 equiv, 25.9 g, 0.15 mol of 68% activity) is added. On complete addition the ice bath is removed and the clear solution is stirred at room temperature for 1 h. The solution is diluted with 250 mL of water and extracted with 2×250 mL portions of CH$_2$Cl$_2$. The combined organic layers are washed with 3×200 mL of 10% aqueous sodium bicarbonate and with 200 mL of water. The organic extracts are dried over sodium sulfate, and concentrated to give an oil, which is used for the next reaction. The preparation is represented by the following reaction:

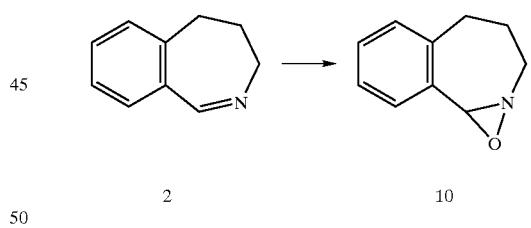

Step 2: Preparation of N-Methyl-1,2-oxydo-1,2,4,5-tetrahydro-3H-2-benzazepinium borontetrafluoride (11):

A 250 mL round-bottomed flask equipped with magnetic stir bar, septum and argon inlet is charged with trimethyloxonium tetrafluoroborate (14.8 g, 0.10 mmol) in CH$_2$Cl$_2$ (30 mL). To the heterogeneous solution cooled to −78° C. (dry ice/acetone bath) is added by cannula a solution of 1,2-oxydo-1,2,4,5-tetrahydro-3H-2-benzazepine (10, 16.1 g, 0.10 mmol) in CH$_2$Cl$_2$ (30 mL). The reaction mixture is allowed to warm to −10° C. (ice/brine bath) and stirred for 2.5 h, at which point the solution is heterogeneous. The solid is collected by filtration and washed with 100 mL of cold (0° C.) CH$_2$Cl$_2$, and dried in a desicator. The preparation is represented by the following reaction:

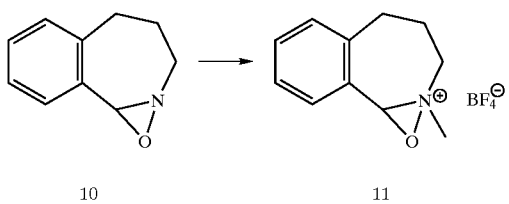

FORMULATION EXAMPLES

Example V

Bleaching detergent compositions having the form of granular laundry detergents are exemplified by the following formulations.

|  | A | B | C | D | E |
|---|---|---|---|---|---|
| Bleach Boosting Compound* | 0.05 | 0.01 | 0.13 | 0.04 | 0.07 |
| Conventional Activator (NOBS) | 0.00 | 2.00 | 1.20 | 0.70 | 0.00 |
| Conventional Activator (TAED) | 3.00 | 0.00 | 2.00 | 0.00 | 0.00 |
| Conventional Activator (NACA-OBS) | 3.00 | 0.00 | 0.00 | 0.00 | 2.20 |
| Sodium Percarbonate | 5.30 | 0.00 | 0.00 | 4.00 | 4.30 |
| Sodium Perborate Monohydrate | 0.00 | 5.30 | 3.60 | 0.00 | 0.00 |
| Linear Alkylbenzenesulfonate | 12.00 | 0.00 | 12.00 | 0.00 | 21.00 |
| C45AE0.6S | 0.00 | 15.00 | 0.00 | 15.00 | 0.00 |
| C2 Dimethylamine N-Oxide | 0.00 | 2.00 | 0.00 | 2.00 | 0.00 |
| C12 Coco Amidopropyl Betaine | 1.50 | 0.00 | 1.50 | 0.00 | 0.00 |
| Palm N-Methyl Glucamide | 1.70 | 2.00 | 1.70 | 2.00 | 0.00 |
| C12 Dimethylhydroxyethyl-ammoniium Chloride | 1.50 | 0.00 | 1.50 | 0.00 | 0.00 |
| AE23-6.5T | 2.50 | 3.50 | 2.50 | 3.50 | 1.00 |
| C25E3S | 4.00 | 0.00 | 4.00 | 0.00 | 0.00 |
| Sodium Tripolyphosphate | 25.00 | 25.00 | 15.00 | 15.00 | 25.00 |
| Zeolite A | 0.00 | 0.00 | 0.00 | 0.00 | 0.00 |
| Acrylic Acid/Maleic Acid Copolymer | 0.00 | 0.00 | 0.00 | 0.00 | 1.00 |
| Polyacrylic Acid, partially neutralized | 3.00 | 3.00 | 3.00 | 3.00 | 0.00 |
| Soil Release Agent | 0.00 | 0.00 | 0.50 | 0.40 | 0.00 |
| Carboxymethylcellulose | 0.40 | 0.40 | 0.40 | 0.40 | 0.40 |
| Sodium Carbonate | 2.00 | 2.00 | 2.00 | 0.00 | 8.00 |
| Sodium Silicate | 3.00 | 3.00 | 3.00 | 3.00 | 6.00 |
| Sodium Bicarbonate | 5.00 | 5.00 | 5.00 | 5.00 | 5.00 |
| Savinase (4T) | 1.00 | 1.00 | 1.00 | 1.00 | 0.60 |
| Termamyl (60T) | 0.40 | 0.40 | 0.40 | 0.40 | 0.40 |
| Lipolase (100T) | 0.12 | 0.12 | 0.12 | 0.12 | 0.12 |
| Carezyme(5T) | 0.15 | 0.15 | 0.15 | 0.15 | 0.15 |
| Diethylenetriaminepenta (methylenephosphonic Acid) | 1.60 | 1.60 | 1.60 | 1.60 | 0.40 |
| Brightener | 0.20 | 0.20 | 0.20 | 0.05 | 0.20 |
| Sulfonated Zinc Phthalocyanine Photobleach | 0.50 | 0.00 | 0.25 | 0.00 | 0.00 |
| $MgSO_4$ | 2.20 | 2.20 | 2.20 | 2.20 | 0.64 |
| $Na_2SO_4$ | balance | balance | balance | balance | balance |

*1-(4,5-dihydro-3H-2-benzazepinium)-propane-3-sulfate prepared according to EXAMPLE I Any of the above compositions is used to launder fabrics at a concentration of 3500 ppm in water, 25° C., and a 15:1 water:cloth ratio. The typical pH is about 9.5 but can be can be adjusted by altering the proportion of acid to Na- salt form of alkylbenzenesulfonate.

Example VI

Bleaching detergent compositions having the form of granular laundry detergents are exemplified by the following formulations.

|  | A | B | C | D | E |
|---|---|---|---|---|---|
| Bleach Boosting Compound* | 0.26 | 0.38 | 0.04 | 0.03 | 0.01 |
| Conventional Activator (NOBS) | 0.00 | 0.00 | 0.00 | 0.50 | 0.00 |
| Conventional Activator (TAED) | 1.80 | 1.00 | 2.50 | 3.00 | 1.00 |
| Conventional Activator (NACA-OBS) | 3.00 | 0.00 | 0.00 | 2.50 | 0.00 |
| Sodium Percarbonate | 5.30 | 0.00 | 0.00 | 9.00 | 0.00 |
| Sodium Perborate Monohydrate | 0.00 | 9.00 | 17.60 | 0.00 | 9.00 |
| Linear Alkylbenzenesulfonate | 21.00 | 12.00 | 0.00 | 12.00 | 12.00 |
| C45AE0.6S | 0.00 | 0.00 | 15.00 | 0.00 | 0.00 |

-continued

|  | A | B | C | D | E |
|---|---|---|---|---|---|
| C2 Dimethylamine N-Oxide | 0.00 | 0.00 | 2.00 | 0.00 | 0.00 |
| C12 Coco Amidopropyl Betaine | 0.00 | 1.50 | 0.00 | 1.50 | 1.50 |
| Palm N-Methyl Glucamide | 0.00 | 1.70 | 2.00 | 1.70 | 1.70 |
| C12 Dimethylhydroxyethylammonium Chloride | 1.00 | 1.50 | 0.00 | 1.50 | 1.50 |
| AE23-6.5T | 0.00 | 2.50 | 3.50 | 2.50 | 2.50 |
| C25E3S | 0.00 | 4.00 | 0.00 | 4.00 | 4.00 |
| Sodium Tripolyphosphate | 25.00 | 15.00 | 25.00 | 15.00 | 15.00 |
| Zeolite A | 0.00 | 0.00 | 0.00 | 0.00 | 0.00 |
| Acrylic Acid/Maleic Acid Copolymer | 0.00 | 0.00 | 0.00 | 0.00 | 0.00 |
| Polyacrylic Acid, partially neutralized | 0.00 | 3.00 | 3.00 | 3.00 | 3.00 |
| Soil Release Agent | 0.30 | 0.50 | 0.00 | 0.50 | 0.50 |
| Carboxymethylcellulose | 0.00 | 0.40 | 0.40 | 0.40 | 0.40 |
| Sodium Carbonate | 0.00 | 2.00 | 2.00 | 2.00 | 2.00 |
| Sodium Silicate | 6.00 | 3.00 | 3.00 | 3.00 | 3.00 |
| Sodium Bicarbonate | 2.00 | 5.00 | 5.00 | 5.00 | 5.00 |
| Savinase (4T) | 0.60 | 1.00 | 1.00 | 1.00 | 1.00 |
| Termamyl (60T) | 0.40 | 0.40 | 0.40 | 0.40 | 0.40 |
| Lipolase (100T) | 0.12 | 0.12 | 0.12 | 0.12 | 0.12 |
| Carezyme(5T) | 0.15 | 0.15 | 0.15 | 0.15 | 0.15 |
| Diethylenetriaminepenta (methylenephosphonic Acid) | 0.40 | 0.00 | 1.60 | 0.00 | 0.00 |
| Brightener | 0.20 | 0.30 | 0.20 | 0.30 | 0.30 |
| Sulfonated Zinc Phthalocyanine Photobleach | 0.25 | 0.00 | 0.00 | 0.00 | 0.00 |
| $MgSO_4$ | 0.64 | 0.00 | 2.20 | 0.00 | 0.00 |
| $Na_2SO_4$ | balance | balance | balance | balance | balance |

*1-(4,5-dihydro-3H-2-benzazepinium)-propane-3-sulfate prepared according to EXAMPLE I.

Any of the above compositions is used to launder fabrics at a concentration of 3500 ppm in water, 25° C., and a 15:1 water:cloth ratio. The typical pH is about 9.5 but can be can be adjusted by altering the proportion of acid to Na- salt form of alkylbenzenesulfonate.

Example VII

A bleaching detergent powder comprises the following ingredients:

| Component | Weight % |
|---|---|
| Bleach Booster* | 0.07 |
| TAED | 2.0 |
| Sodium Perborate Tetrahydrate | 10 |
| $C_{12}$ linear alkyl benzene sulfonate | 8 |
| Phosphate (as sodium tripolyphosphate) | 9 |
| Sodium carbonate | 20 |
| Talc | 15 |
| Brightener, perfume | 0.3 |
| Sodium Chloride | 25 |
| Water and Minors* | Balance to 100% |

*N-Methyl-4,5-dihydro-3H-2-benzazepinium borontetrafluoride prepared according to EXAMPLE II.

Example VIII

A laundry bar suitable for hand-washing soiled fabrics is prepared by standard extrusion processes and comprises the following:

| Component | Weight % |
|---|---|
| Bleach Booster[1] | 0.1 |
| TAED | 1.7 |
| NOBS | 0.2 |
| Sodium Percarbonate | 12 |
| $C_{12}$ linear alkyl benzene sulfonate | 30 |
| Phosphate (as sodium tripolyphosphate) | 10 |
| Sodium carbonate | 5 |
| Sodium pyrophosphate | 7 |
| Coconut monoethanolamide | 2 |
| Zeolite A (0.1–10 micron) | 5 |
| Carboxymethylcellulose | 0.2 |
| Polyacrylate (m.w. 1400) | 0.2 |
| Brightener, perfume | 0.2 |
| Protease | 0.3 |
| $CaSO_4$ | 1 |
| $MgSO_4$ | 1 |
| Water | 4 |
| Filler[2] | Balance to 100% |

[1]N-Methyl-4,5-dihydro-3H-2-benzazepinium borontetrafluoride prepared according to EXAMPLE II.
[2]Can be selected from convenient materials such as $CaCO_3$, talc, clay, silicates, and the like.
Acidic fillers can be used to reduce pH.

The composition is used to launder fabrics at a concentration in solution of about 1000 ppm at a temperature of 20–40° C. and a water to fabric ratio of about 20:1.

Example IX

A laundry detergent composition suitable for machine use is prepared by standard methods and comprises the following composition.

| Component | Weight % |
|---|---|
| Bleach Booster* | 0.20 |
| NOBS | 7.20 |
| Sodium Perborate Tetrahydrate | 9.2 |
| Sodium Carbonate | 23.74 |
| Anionic surfactant | 14.80 |
| Alumino Silicate | 21.30 |
| Silicate | 1.85 |
| Diethylenetriaminepentacetic acid | 0.43 |
| Polyacrylic acid | 2.72 |
| Brightener | 0.23 |
| Polyethylene glycol solids | 1.05 |
| Sulfate | 8.21 |
| Perfume | 0.25 |
| Water | 7.72 |
| Processing aid | 0.10 |
| Miscellaneous | 0.43 |

*1-(8-chloro-3,4-dihydro-1-methyl-6-phenyl-1H-1,5-benzodiazocin-2-one) hexane-2-sulfate prepared according to EXAMPLE III.

The composition is used to launder fabrics at a concentration in solution of about 1000 ppm at a temperature of 20–40° C. and a water to fabric ratio of about 20:1.

Example X

| Component | Weight % |
|---|---|
| Bleach Booster* | 0.07 |
| NOBS | 6.0 |
| Sodium Perborate Tetrahydrate | 8.0 |
| Sodium Carbonate | 21.0 |
| Anionic surfactant | 12.0 |
| Alumino Silicate | 18.0 |
| Diethylenetriaminepentacetic acid | 0.3 |
| Nonionic surfactant | 0.5 |
| Polyacrylic acid | 2.0 |
| Brightener | 0.3 |
| Sulfate | 17.0 |
| Perfume | 0.25 |
| Water | 6.7 |
| Miscellaneous | 2.95 |

*1-(4,5-dihydro-3H-2-benzazepinium)-propane-3-sulfate prepared according to EXAMPLE I.

The composition is used as a laundry auxiliary for laundering fabrics at a concentration in solution of about 850 ppm at a temperature of 2040° C. and a water to fabric ratio of about 20:1.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

The compositions of the present invention can be suitably prepared by any process chosen by the formulator, non-limiting examples of which are described in U.S. Pat. Nos. 5,691,297; 5,574,005; 5,569,645; 5,565,422; 5,516,448; 5,489,392; and 5,486,303.

In addition to the above examples, the bleach systems of the present invention can be formulated into any suitable laundry detergent composition, non-limiting examples of which are described in U.S. Pat. Nos. 5,679,630; 5,565,145; 5,478,489; 5,470,507; 5,466,802; 5,460,752; 5,458,810; 5,458,809; and 5,288,431.

Having described the invention in detail with reference to preferred embodiments and the examples, it will be clear to those skilled in the art that various changes and modifications may be made without departing from the scope of the invention and the invention is not to be considered limited to what is described in the specification.

What is claimed is:

1. A bleaching composition comprising a bleach boosting compound in conjunction with or without a peroxygen source, wherein said bleach boosting compound is selected from the group consisting of:

aryliminium cations, aryliminium zwitterions, aryliminium polyions having a net charge of from about +3 to about −3 and mixtures thereof, said bleach booster being represented by the formulas [I] and [II]:

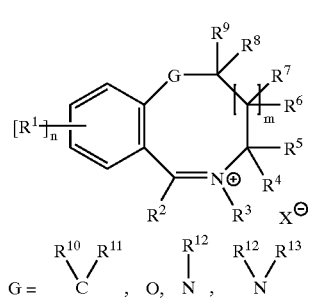

[I]

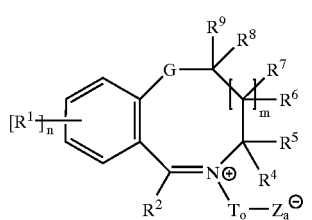

[II]

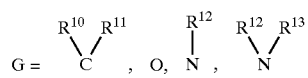

wherein: m is 0 or 1 and wherein n is an integer from 0 to 4; each $R^1$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^1$ substituents may combine to form a fused aryl, fused carbocyclic or fused heterocyclic ring; $R^2$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^3$ may be a substituted or unsubstituted, saturated or unsaturated, radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of $-CO_2^-$, $-SO_3^-$, $-OSO_3^-$, $-SO_2^-$ and $-OSO_2^-$ and a is either 1 or 2; $T_o$ is selected from the group consisting of: (1) $-(CH(R^{14}))-$ or $-(C(R^{14})_2)-$ wherein $R^{14}$ is independently selected from H or $C_1$–$C_8$ alkyl; (2) $-CH_2(C_6H_4)-$;

(3)

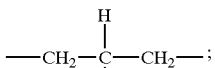

(4)

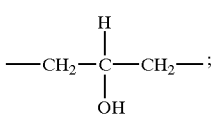

(5) $-(CH_2)_d(E)(CH_2)_f-$ wherein d is from 2 to 8, f is from 1 to 3 and E is $-C(O)O-$;

(6) $-C(O)NR^{15}-$ wherein $R^{15}$ is H or $C_1$–$C_4$ alkyl;

(7)

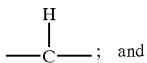 ; and (8)

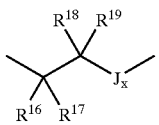

wherein x is equal to 0–3; J, when present, is independently selected from the group consisting of $-CR^{20}R^{21}-$, $-CR^{20}R^{21}CR^{22}R^{23}-$, and $-CR^{20}R^{21}CR^{22}R^{23}CR^{24}R^{25}-$; $R^{16}$–$R^{25}$ are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^4$–$R^{11}$ are substituted or unsubstituted radicals independently selected from the group consisting of H, linear or branched $C_1$–$C_{12}$ alkyls, alkylenes, alkoxys, aryls, alkaryls, aralkyls, cycloalkyls, and heterocyclic rings, and $R^{12}$ and $R^{13}$ are substituted or unsubstituted radicals independently selected from the group consisting of H, oxygen, linear or branched $C_1$–$C_{12}$ alkyls, alkylenes, alkoxys, aryls, alkaryls, aralkyls, cycloalkyls, and heterocyclic rings; provided that any of $R^1$–$R^{13}$ may be joined together with any other of $R^1$–$R^{13}$ to form part of a common ring; any geminal $R^4$–$R^{11}$ may combine to form a carbonyl; any vicinal $R^4$–$R^{13}$ may join to form unsaturation; and wherein any one group of substituents $R^4$–$R^7$, $R^6$–$R^9$, or $R^8$–$R^{13}$ may combine to form a substituted or unsubstituted fused unsaturated moiety;

(b) a bleaching species selected from the group consisting of oxaziridinium cations, oxaziridinium zwitterions, oxaziridinium polyions having a net charge of from about +3 to about −3, and mixtures thereof, said oxaziridinium compound being represented by the formulas [III] and [IV]:

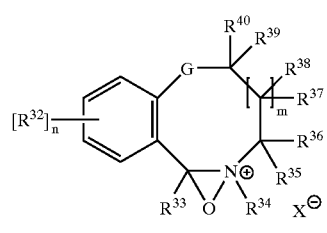

[III]

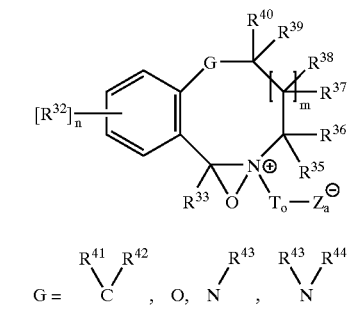

[IV]

wherein: m is 0 or 1 and wherein n is an integer from 0 to 4; provided that when m is equal to 0, G does not equal $R^{41}$—C—$R^{42}$ each $R^{32}$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^{32}$ substituents may combine to form a fused aryl, fused carbocyclic or fused heterocyclic ring; $R^{33}$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^{34}$ may be a substituted or unsubstituted radical selected from the group consisting of H, alkyl, cycloalkyl, alkaryl, aryl, aralkyl, heterocyclic ring, and a radical represented by the formula:

-$T_o$-$(Z^-)_a$ where $Z^-$ is covalently bonded to $T_o$, and $Z^-$ is selected from the group consisting of —$CO_2^-$, —$SO_3^-$, —$OSO_3^-$, —$SO_2^-$ and —$OSO_2^-$ and a is either 1 or 2; $T_o$ is selected from the group consisting of (1) —(CH($R^{45}$))— or —(C($R^{45}$)$_2$)— wherein $R^{45}$ is independently selected from H or $C_1$–$C_8$ alkyl; (2) —$CH_2(C_6H_4)$—; (3) —$(CH_2)_d(E)(CH_2)_f$— wherein d is from 2 to 8, f is from 1 to 3 and E is —C(O)O—; (4) —C(O)N$R^{46}$— wherein $R^{46}$ is H or $C_1$–$C_4$ alkyl; and

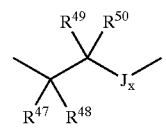

(5)

wherein x is equal to 0–3; J, when present, is independently selected from the group consisting of —C$R^{51}R^{52}$—, —C$R^{51}R^{52}$C$R^{53}R^{54}$—, and —C$R^{51}R^{52}$C$R^{53}R^{54}$C$R^{55}R^{56}$—; $R^{47}$–$R^{56}$ are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^{35}$–$R^{42}$ are substituted or unsubstituted radicals independently selected from the group consisting of H, linear or branched $C_1$–$C_{12}$ alkyls, alkylenes, alkoxys, aryls, alkaryls, aralkyls, cycloalkyls, and heterocyclic rings, and $R^{43}$ and $R^{44}$ are substituted or unsubstituted radicals independently selected from the group consisting of H, oxygen, linear or branched $C_1$–$C_{12}$ alkyls, alkylenes, alkoxys, aryls, alkaryls, aralkyls, cycloalkyls, and heterocyclic rings, further provided that any of $R^{32}$–$R^{44}$ may be joined together with any other of $R^{32}$–$R^{44}$ to form part of a common ring; any vicinal $R^{35}$–$R^{44}$ may join to form unsaturation; and wherein any one group of substituents $R^{35}$–$R^{38}$, $R^{37}$–$R^{40}$, $R^{39}$–$R^{42}$ or $R^{43}$ and $R^{44}$, when present, may combine to form a substituted or unsubstituted fused unsaturated moiety; and mixtures thereof.

2. The bleaching composition as claimed in claim 1 wherein said bleach boosting compound comprises from about 0.001% to about 10% by weight of said composition, and said peroxygen source, when present, comprises from about 0.01% to about 60% by weight of said composition.

3. The bleaching composition as claimed in claim 1 wherein said peroxygen source, when present, is selected from the group consisting of:

(a) preformed peracid compounds selected from the group consisting of percarboxylic acids and salts, percarbonic acids and salts, perimidic acids and salts, peroxymonosulfuric acids and salts, and mixtures thereof, and (b) hydrogen peroxide sources selected from the group consisting of perborate compounds, percarbonate compounds, perphosphate compounds and mixtures thereof, and with or without a bleach activator.

4. The bleaching composition as claimed in claim 1 wherein said bleaching species is an oxaziridinium cation wherein $R^{34}$ is selected from the group consisting of linear or branched C1–C14 substituted or unsubstituted alkyls, or said bleaching species is an oxaziridinium zwitterion wherein $R^{34}$ is a radical represented by the formula:

-$T_o$-$(Z^-)_a$ wherein $Z^-$ is $-CO_2^-$, $-SO_3^-$ or $-OSO_3^-$, a is 1 and $T_o$ is selected from the group consisting of:

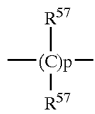

wherein p is an integer from 2 to 4, and $R^{57}$ is independently selected from the group consisting of H and linear or branched $C_1-C_{18}$ substituted or unsubstituted alkyl and cycloalkyl.

5. The bleaching composition as claimed in claim 1 wherein said bleaching species is an oxaziridinium polyion having a net negative charge wherein $R^{33}$ is H, $Z^-$ is $-CO_2^-$, $-SO_3^-$ or $-OSO_3^-$ and a is 2.

6. The bleaching composition as claimed in claim 1 wherein said bleaching species is an oxaziridinium polyion having a net negative charge wherein $R^{33}$ is H and $R^{34}$ is selected from the group consisting of a radical represented by the formula:

wherein $Z^-$ is $-CO_2^-$, $-SO_3^-$ or $-OSO_3^-$, a is 1 and $T_o$ is selected from the group consisting of:

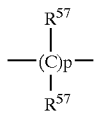

wherein p is an integer from 2 to 4, and $R^{57}$ is independently selected from the group consisting of H and linear or branched $C_1-C_{18}$ substituted or unsubstituted alkyl and cycloalkyl.

7. The bleaching composition as claimed in claim 1 wherein said bleaching composition further comprises a surfactant.

8. The bleaching composition as claimed in claim 7 wherein said surfactant is an anionic surfactant.

9. The bleaching composition as claimed in claim 1 wherein said bleaching composition further comprises an enzyme.

10. The bleaching composition as claimed in claim 1 wherein said bleaching composition further comprises a chelating agent.

11. A cationic or zwitterionic laundry bleach boosting compound selected from the group consisting of:

[I]

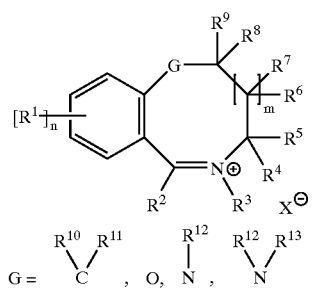

-continued

[II]

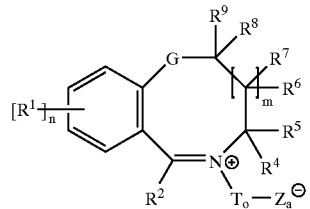

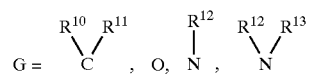

[III]

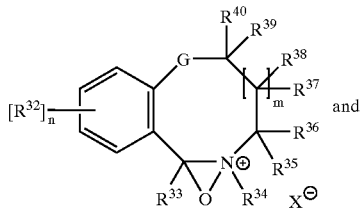

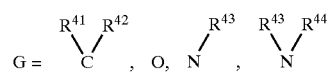

and

[IV]

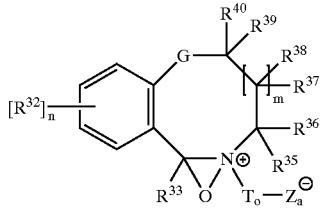

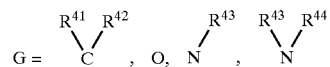

wherein m is 0 or 1 and wherein n is an integer from 0 to 4, provided that when m is equal to 0, G does not equal $R^{41}-C-R^{42}$; each $R^{32}$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^{32}$ substituents may combine to form a fused aryl, fused carbocyclic or fused heterocyclic ring; $R^{33}$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^{34}$ may be a substituted or unsubstituted radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of $-CO_2$, $-SO_3^-$, $-OSO_3^-$, $-SO2^-$ and $-OSO_2^-$ and a is either 1 or 2; $T_o$ is selected from the group consisting of: (1) $-(CH(R^{45}))-$ or $-C(R^{45})_2)-$ wherein $R^{45}$ is independently selected from H or $C_1-C_8$ alkyl; (2) $-CH_2(C_6H_4)-$; (3) $-(CH_2)_d(E)(CH_2)_f$ wherein d is from 2 to 8, f is from 1 to 3 and E is $-C(O)O-$; (4) $-C(O)NR^{46}-$ wherein $R^{46}$ is H or $C_1-C_4$ alkyl; and (5)

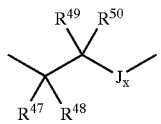

wherein x is equal to 0–3; J, When present, is independently selected from the group consisting of —$CR^{51}R^{52}$—, —$CR^{51}R^{52}R^{53}R^{54}$—, and —$CR^{51}R^{52}CR^{53}R^{54}CR^{55}R^{56}$—; are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^{35}$–$R^{42}$ are substituted or unsubstituted radicals independently selected from the group consisting of H, linear or branched $C_1$–$C_{12}$ alkyl, alkylenes, alkoxys, aryls, alkaryls, aralkyls, cycloalkyls, and heterocyclic rings, and $R^{43}$ and $R^{44}$ are substituted or unsubstituted radicals independently selected from the group consisting of H, oxygen, linear or branched $C_1$–$C_{12}$ alkyls, alkylenes, alkoxys, aryl, alkaryls, aralkyls, cycloalkyls, and heterocyclic rings further provided that any of $R^{32}$–$R^{44}$ may be joined together with any other of $R^{32}$–$R^{44}$ to form part of a common ring; any vicinal $R^{35}$–$R^{44}$ may join to form unsaturation; and wherein any one group of substituents $R^{35}$–$R^{38}$, $R^{37}$–$R^{40}$, $R^{39}$–$R^{42}$ or $R^{43}$ and $R^{44}$, when present, may combine to form a substituted or unsubstituted fused unsaturated moiety.

12. A method for laundering a fabric in need of laundering, said method comprising contacting said fabric with a laundry solution having a bleaching composition according to claim 1.

13. A method according to claim 12 wherein the in-use concentration for said bleach boosting compound is from about 0.01 ppm to about 10 ppm.

14. A method according to claim 13 wherein the in-use concentration for said bleach boosting compound is from about 0.04 ppm to about 2.5 ppm.

15. A method according to claim 14 wherein the in-use concentration for said bleach boosting compound is from about 0.1 ppm to about 1 ppm.

16. A laundry additive product comprising a bleach boosting compound selected from the group consisting of:

aryliminium cations, aryliminium zwitterions, aryliminium polyions having a net charge of from about +3 to about −3 and mixtures thereof, said bleach booster being represented by the formulas [I] and [II]:

[I]

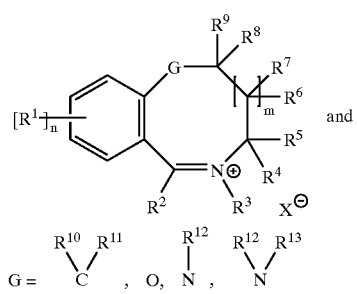

and

[II]

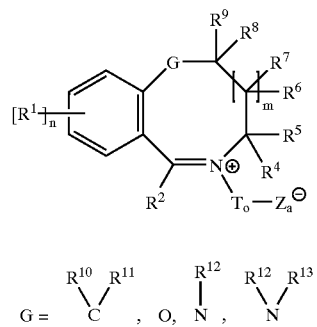

-continued

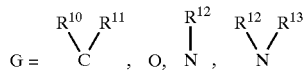

wherein: m is 0 or 1 and wherein n is an integer from 0 to 4; each $R^1$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^1$ substituents may combine to form a fused aryl, fused carbocyclic or fused heterocyclic ring; $R^2$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^3$ may be a substituted or unsubstituted, saturated or unsaturated radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of —$CO_2^-$, —$SO_3^-$, —$OSO_3^-$, —$SO_2^-$ and —$OSO_2^-$ and a is either 1 or 2; $T_o$ is selected from the group consisting of: (1) —$(CH(R^{14}))$— or —$(C(R^{14})_2)$— wherein $R^{14}$ is independently selected from H or $C_1$–$C_8$ alkyl; (2) —$CH_2(C_6H_4)$—;

(3)

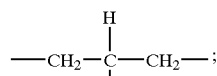

(4)

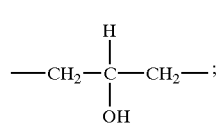

(5) —$(CH_2)_d(E)(CH_2)_f$— wherein d is from 2 to 8, f is from 1 to 3 and E is —C(O)O—;

(6) —$C(O)NR^{15}$— wherein $R^{15}$ is H or $C_1$–$C_4$ alkyl;

(7)

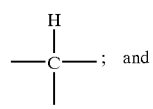

; and (8)

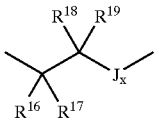

wherein x is equal to 0–3; J, when present, is independently selected from the group consisting of —$CR^{20}R^{21}$—, —$CR^{20}R^{21}CR^{22}R^{23}$—, and —$CR^{20}R^{21}CR^{22}R^{23}CR^{24}R^{25}$—; $R^{16}$–$R^{25}$ are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^4$–$R^{11}$ are substituted or unsubstituted radicals independently selected from the group consisting of H, linear or branched $C_1$–$C_{12}$ alkyls, alkylenes, alkoxys, aryls, alkaryls, aralkyls, cycloalkyls, and heterocyclic rings, and $R^{12}$ and $R^{13}$ are substituted or unsubstituted radicals independently selected from the group consisting of H, oxygen, linear or branched $C_1$–$C_{12}$ alkyls, alkylenes, alkoxys, aryls, alkaryls, aralkyls, cycloalkyls, and heterocyclic rings; provided that any of $R^1$–$R^{13}$ may be joined together with any other of $R^1$–$R^{13}$ to form part of a common ring; any geminal $R^4$–$R^{11}$ may combine to form a carbonyl; any vicinal $R^4$–$R^{13}$ may join to form unsaturation; and wherein any one group of substituents $R^4$–$R^7$, $R^6$–$R^9$, or $R^8$–$R^{13}$ may combine to form a substituted or unsubstituted fused unsaturated moiety;

(b) a bleaching species selected from the group consisting of oxaziridinium cations, oxaziridinium zwitterions, oxaziridinium polyions having a net charge of from about +3 to about −3, and mixtures thereof, said oxaziridinium compound being represented by the formulas [III] and [IV]:

[III]

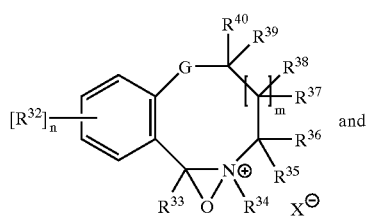

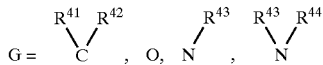

[IV]

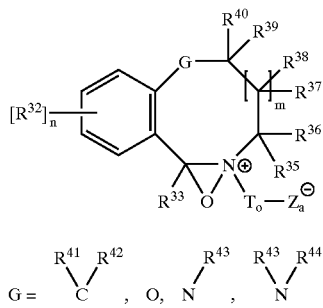

wherein: m is 0 or 1 and wherein n is an integer from 0 to 4; provided that when m is equal to 0, G does not equal $R^{41}$—C—$R^{42}$ each $R^{32}$ is independently selected from a substituted or unsubstituted radical selected from the group consisting of H, alkyl, cycloalkyl, aryl, fused aryl, heterocyclic ring, fused heterocyclic ring, nitro, halo, cyano, sulfonato, alkoxy, keto, carboxylic, and carboalkoxy radicals, and any two vicinal $R^{32}$ substituents may combine to form a fused aryl, fused carbocyclic or fused heterocyclic ring; $R^{33}$ may be a substituted or unsubstituted radical selected from the group consisting of H, alkyl, cycloalkyl, alkaryl, aryl, aralkyl, heterocyclic ring, nitro, halo, cyano, sulfonato, alkoxy, keto, carboxylic, and carboalkoxy radicals; $R^{34}$ may be a substituted or unsubstituted radical selected from the group consisting of H, alkyl, cycloalkyl, alkaryl, aryl, aralkyl, heterocyclic ring, and a radical represented by the formula:

where $Z^-$ is covalently bonded to $T_o$, and $Z^-$ is selected from the group consisting of —$CO_2^-$, —$SO_3^-$, —$OSO_3^-$, —$SO_2^-$ and —$OSO_2^-$ and a is either 1 or 2; $T_o$ is selected from the group consisting of: (1) —$(CH(R^{45}))$— or —$(C(R^{14})_2)$— wherein $R^{45}$ is independently selected from $C_1$–$C_8$ alkyl; (2) —$CH_2(C_6H_4)$—; (3) —$(CH_2)_d(E)(CH_2)_f$— wherein d is from 2 to 8, f is from 1 to 3 and E is —$C(O)O$—; (4) —$C(O)NR^{46}$— wherein $R^{46}$ is H or $C_1$–$C_4$ alkyl; and (5)

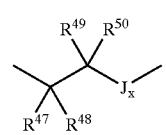

wherein x is equal to 0–3; J, when present, is independently selected from the group consisting of —$CR^{51}R^{52}$—, —$CR^{51}R^{52}CR^{53}R^{54}$—, and —$CR^{51}R^{52}CR^{53}R^{54}CR^{55}R^{56}$—; $R^{47}$–$R^{56}$ are substituted or unsubstituted radicals selected from the linear or branched group consisting of H, $C_1$–$C_{18}$ alkyls, cycloalkyls, alkaryls, aryls, aralkyls, alkylenes, heterocyclic rings, alkoxys, arylcarbonyls, carboxyalkyls and amide groups; $R^{35}$–$R^{42}$ are substituted or unsubstituted independently selected from the group consisting of H, linear or branched $C_1$–$C_{12}$ alkyls, alkylenes, alkoxys, aryls, alkaryls, aralkyls, cycloalkyls, and heterocyclic rings, and $R^{43}$ and $R^{44}$ are substituted or unsubstituted radicals independently selected from the group consisting of H, oxygen, linear or branched $C_1$–$C_{12}$ alkyls, alkylenes, alkoxys, aryls, alkaryls, aralkyls, cycloalkyls, and heterocyclic rings, further provided that any of $R^{32}$–$R^{44}$ may be joined together with any other of $R^{32}$–$R^{44}$ to form part of a common ring; any vicinal $R^{35}$–$R^{44}$ may join to form unsaturation; and wherein any one group of substituents $R^{35}$–$R^{38}$, $R^{37}$–$R^{40}$, $R^{39}$–$R^{42}$ or $R^{43}$ and $R^{44}$, when present, may combine to form a substituted or unsubstituted fused unsaturated moiety; and mixtures thereof.

17. The laundry additive product as claimed in claim 16 wherein said laundry additive product is in a dosage from selected from the group consisting of a pill, tablet, caplet, gelcap or other single dosage form.

18. The laundry additive product as claimed in claim 16 wherein said laundry additive product further includes a suitable carrier.

19. The bleaching composition as claimed in claim 3 wherein said bleach activator is selected from the group consisting of: tetraacetyl ethylene diamine (TAED); benzoylcaprolactam (BzCL); 4-nitrobenzoylcaprolactam; 3-chlorobenzoylcaprolactam; benzoyloxybenzenesulphonate (BOBS); nonanoyloxybenzenesulphonate (NOBS); phenyl benzoate (PhBz); decanoyloxybenzenesulphonate ($C_{10}$-OBS); benzoylvalerolactam (BZVL); octanoyloxybenzenesulphonate ($C_8$-OBS); perhydrolyzable esters; 4-[N-(nonaoyl) amino hexanoyloxy]-benzene sulfonate sodium salt (NACA-OBS); lauroyloxybenzenesulfonate (LOBS or $C_{12}$-OBS); 10-undecenoyloxybenzenesulfonate (UDOBS); decanoyloxybenzoic acid (DOBA) and mixtures thereof.

* * * * *